United States Patent
Sugie et al.

(10) Patent No.: US 10,634,891 B2
(45) Date of Patent: Apr. 28, 2020

(54) MEDICAL OBSERVATION DEVICE, LENS DRIVING CONTROL DEVICE, LENS DRIVING CONTROL METHOD, AND VIDEO MICROSCOPE DEVICE

(71) Applicant: SONY CORPORATION, Tokyo (JP)

(72) Inventors: Yuki Sugie, Kanagawa (JP); Takeshi Uemori, Tokyo (JP); Kenji Takahasi, Kanagawa (JP); Daisuke Tsuru, Chiba (JP)

(73) Assignee: SONY CORPORATION, Tokyo (JP)

( * ) Notice: Subject to any disclaimer, the term of this patent is extended or adjusted under 35 U.S.C. 154(b) by 124 days.

(21) Appl. No.: 15/559,552

(22) PCT Filed: Mar. 2, 2016

(86) PCT No.: PCT/JP2016/056509
§ 371 (c)(1),
(2) Date: Sep. 19, 2017

(87) PCT Pub. No.: WO2016/158184
PCT Pub. Date: Oct. 6, 2016

(65) Prior Publication Data
US 2018/0045934 A1    Feb. 15, 2018

(30) Foreign Application Priority Data

Mar. 31, 2015 (JP) .................... 2015-073832

(51) Int. Cl.
*G02B 21/18* (2006.01)
*G02B 21/00* (2006.01)
(Continued)

(52) U.S. Cl.
CPC .......... *G02B 21/006* (2013.01); *A61B 1/0002* (2013.01); *A61B 1/00006* (2013.01);
(Continued)

(58) Field of Classification Search
None
See application file for complete search history.

(56) References Cited

U.S. PATENT DOCUMENTS 4,447,719 A * 5/1984 Ogasawara .............. G02B 7/34
250/204
8,213,786 B2 * 7/2012 Song ...................... G03B 13/32
396/121

(Continued)

FOREIGN PATENT DOCUMENTS

JP    7-15749 A      1/1995
JP    2002-85330 A   3/2002
(Continued)

OTHER PUBLICATIONS

International Search Report and Written Opinion of PCT Application No. PCT/JP2016/056509, dated May 31, 2016, 09 pages of ISRWO.

*Primary Examiner* — Christopher G Findley
(74) *Attorney, Agent, or Firm* — Chip Law Group

(57) ABSTRACT

A medical observation device that includes an evaluation value calculation unit configured to calculate a focus evaluation value indicating a focus state of a lens for each of two or more lenses, and a movement control unit configured to specify a lens movement parameter that is common to the two or more lenses on the basis of the focus evaluation value.

13 Claims, 26 Drawing Sheets

(51) Int. Cl.
    *H04N 5/232*     (2006.01)
    *G02B 23/24*     (2006.01)
    *A61B 90/20*     (2016.01)
    *A61B 1/00*     (2006.01)
    *A61B 1/04*     (2006.01)
    *H04N 5/225*     (2006.01)
    *A61B 90/00*     (2016.01)

(52) U.S. Cl.
    CPC ...... *A61B 1/00009* (2013.01); *A61B 1/00045* (2013.01); *A61B 1/00188* (2013.01); *A61B 1/00193* (2013.01); *A61B 1/04* (2013.01); *A61B 90/20* (2016.02); *G02B 21/008* (2013.01); *G02B 21/0028* (2013.01); *G02B 23/2415* (2013.01); *G02B 23/2484* (2013.01); *H04N 5/23212* (2013.01); *A61B 2090/371* (2016.02); *G06T 2207/10068* (2013.01); *H04N 2005/2255* (2013.01)

(56) References Cited

U.S. PATENT DOCUMENTS

2014/0307072 A1* 10/2014 Takahashi .......... H04N 5/23296
                                                      348/65
2015/0160448 A1* 6/2015 Hong .................. G02B 21/22
                                                      348/47

FOREIGN PATENT DOCUMENTS

| JP | 2002-267919 A | 9/2002 |
| JP | 2014-137323 A | 7/2014 |

\* cited by examiner

FIG. 7

| USER ID | A | B | C | D |
|---|---|---|---|---|
| SELECTION INFORMATION | LEFT | RIGHT | RIGHT | LEFT |

FIG. 17
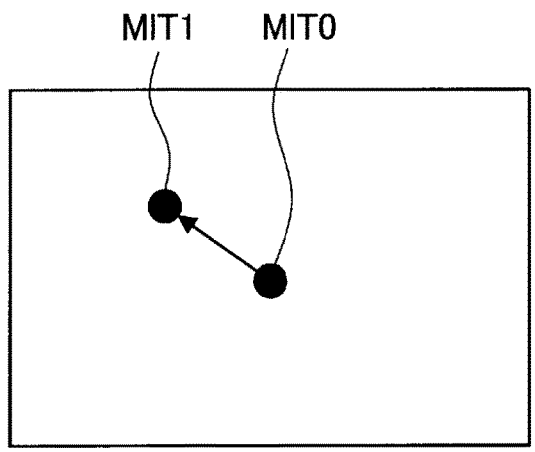
L CAMERA SENSOR
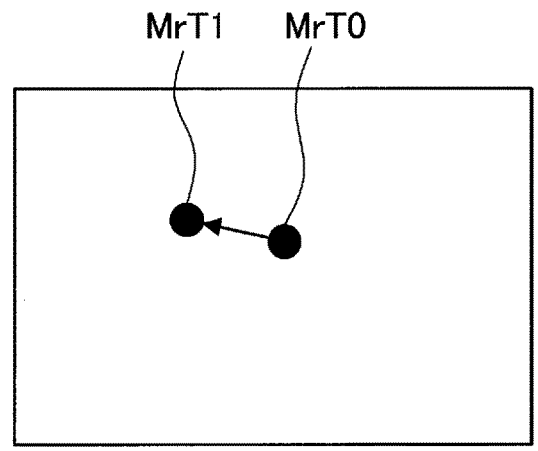
R CAMERA SENSOR

MEDICAL OBSERVATION DEVICE, LENS DRIVING CONTROL DEVICE, LENS DRIVING CONTROL METHOD, AND VIDEO MICROSCOPE DEVICE

CROSS REFERENCE TO RELATED APPLICATIONS

This application is a U.S. National Phase of International Patent Application No. PCT/JP2016/056509 filed on Mar. 2, 2016, which claims priority benefit of Japanese Patent Application No. JP 2015-073832 filed in the Japan Patent Office on Mar. 31, 2015. Each of the above-referenced applications is hereby incorporated herein by reference in its entirety.

TECHNICAL FIELD

The present disclosure relates to a medical observation device, a lens driving control device, a lens driving control method, a program, and a video microscope device.

BACKGROUND ART

Endoscope devices with slender insertion units that can be inserted into body cavities of patients and the like to enable lesions that are not directly visible by eye to be observed have been widely used in the medical field and the like in the past. For example, Patent Literature 1 and Patent Literature 2 disclose endoscope devices by which stereoscopic images can be acquired using two or more cameras in order to precisely observe lesions.

CITATION LIST

Patent Literature

Patent Literature 1: JP 2002-85330A
Patent Literature 2: JP 2005-334462A

DISCLOSURE OF INVENTION

Technical Problem

It has been demanded that such endoscope devices be able to perform proper focus adjustment (focusing).

Solution to Problem

According to the present disclosure, there is provided a medical observation device including: an evaluation value calculation unit configured to calculate a focus evaluation value indicating a focus state of a lens for each of two or more lenses; and a movement control unit configured to specify a lens movement parameter that is common to the two or more lenses on the basis of the focus evaluation value.

Further, according to the present disclosure, there is provided a lens driving control device including: an evaluation value calculation unit configured to calculate a focus evaluation value indicating a focus state of a lens for each of two or more lenses; and a movement control unit configured to specify a lens movement parameter that is common to the two or more lenses on the basis of the focus evaluation value.

Further, according to the present disclosure, there is provided a lens driving control method including: calculating a focus evaluation value indicating a focus state of a lens for each of two or more lenses; and specifying, by a processor, a lens movement parameter that is common to the two or more lenses on the basis of the focus evaluation value.

Further, according to the present disclosure, there is provided a program causing a computer to perform: a process of calculating a focus evaluation value indicating a focus state of a lens for each of two or more lenses; and a process of specifying, by a processor, a lens movement parameter that is common to the two or more lenses on the basis of the focus evaluation value.

Further, according to the present disclosure, there is provided a video microscope device including: an evaluation value calculation unit configured to calculate a focus evaluation value indicating a focus state of a lens for each of two or more lenses; a movement control unit configured to specify a lens movement parameter that is common to the two or more lenses on the basis of the focus evaluation value; and an imaging unit including an image sensor. The imaging unit captures a microscopic image.

Further, according to the present disclosure, there is provided a medical observation device including: an evaluation value calculation unit configured to calculate a focus evaluation value indicating a focus state of a lens for each of two or more lenses; a selection unit configured to select one reference lens from the two or more lenses; and a movement control unit configured to specify a lens movement parameter for each of the two or more lenses on the basis of the focus evaluation value. The evaluation value calculation unit sets a method for calculating the focus evaluation value corresponding to a lens other than the reference lens on the basis of the focus evaluation value corresponding to the reference lens.

Advantageous Effects of Invention

According to the present disclosure described above, it is possible to perform proper focus adjustment.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 7 is a table showing an example of user information stored by a storage unit in the modified example according to the embodiment.

FIG. 17 is an illustrative diagram for describing the overview of camera shake correction according to the embodiment.

MODE(S) FOR CARRYING OUT THE INVENTION

Figure 1:
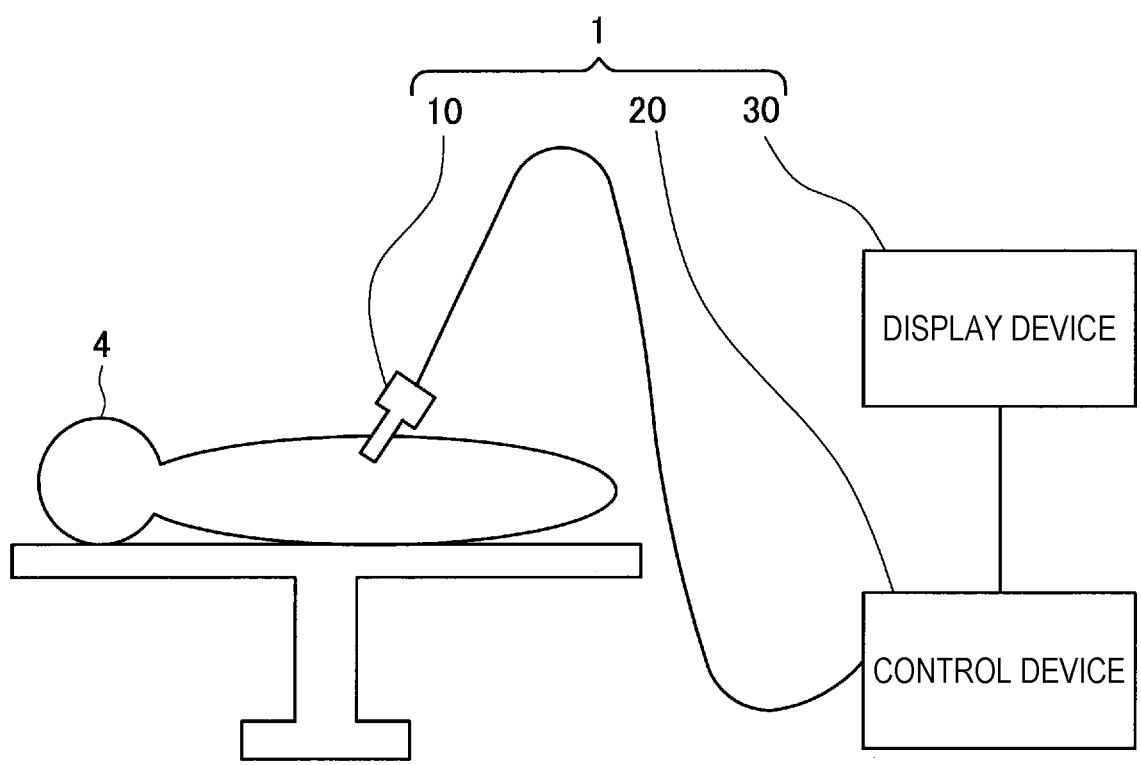
FIG. 1 is an illustrative diagram showing an overview of a medical observation system 1 according to a first embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that, in this description and the drawings, structural elements that have substantially the same function and structure are sometimes distinguished from each other using different alphabets after the same reference sign. However, when there is no need in particular to distinguish structural elements that have substantially the same function and structure, the same reference sign alone is attached.

Note that description will be provided in the following manner.

<<1. First embodiment>>
<1-1. Overview of first embodiment>
<1-2. Configuration of first embodiment>
<1-3. Operation of first embodiment>
<1-4. Effect of first embodiment>
<1-5. Modified examples of first embodiment>
<<2. Second embodiment>>
<2-1. Overview of second embodiment>
<2-2. Configuration of second embodiment>
<2-3. Operation of second embodiment>
<2-4. Effect of second embodiment>
<<3. Third embodiment>>
<3-1. Overview of third embodiment>
<3-2. Configuration of third embodiment>
<3-3. Operation of third embodiment>
<3-4. Effect of third embodiment>
<3-5. Modified examples of third embodiment>
<<4. Example of hardware configuration>>
<<5. Conclusion>>

1. First Embodiment

1-1. Overview of First Embodiment

First, an overview of a medical observation system according to a first embodiment of the present disclosure will be described with reference to a drawing. FIG. 1 is an illustrative diagram showing the overview of the medical observation system according to the first embodiment of the present disclosure.

The medical observation system 1 according to the first embodiment of the present disclosure includes an endoscope device 10, a control device 20, and a display device 30, as shown in FIG. 1. The endoscope device 10 is primarily inserted into a body cavity of a patient 4, the control device 20 performs control of the endoscope device 10 and various processes, and the display device 30 displays a video of the body cavity of the patient 4, as shown in FIG. 1.

The endoscope device 10 has two or more cameras therein, and the display device 30 displays a left-eye image and a right-eye image that are stereoscopically visible. These stereoscopically visible images enable a user to ascertain a more precise condition of the body cavity of the patient 4.

The endoscope device having a lens driving control mechanism shared by the two or more camera uses, for example, a focus adjusting lens of one of the cameras as a reference lens and performs focus adjustment by moving a focus adjusting lens of another camera in accordance with a movement of the reference lens. Here, although positions of focus adjusting lenses of the cameras are adjusted in advance in a course of manufacturing, it is hard to prevent an error from occurring between the cameras despite the adjustment. For that reason, when focus adjustment is performed using the reference lens, there may be a case in which a camera other than the camera having the reference lens fails to highly accurately adjust focus, a low quality image is captured, and as a result, different image qualities of images are presented to the left and right eyes of a user. In particular, medical equipment such as an endoscope device and the like is used mostly in close proximity to a subject, which leads to concern that a minor error between cameras develops into a significant difference in image quality.

Meanwhile, there is a research result with respect to a sense of vision of human beings showing that human beings have different dominant eyes and that human beings can perceive stereoscopic images more comfortably when a higher quality image is presented to their dominant eyes than when a lower quality image is presented to the dominant eyes. However, with respect to past endoscope devices, such a reference lens is set in advance, for example, in a design or manufacturing stage, and only a focus state of the pre-set reference lens can be evaluated. However, a lens corresponding to a dominant eye of a user is not set as the reference lens at all times. Thus, there is concern of low quality images being presented to a dominant eye of a user, which hinders the user from comfortably perceiving a stereoscopic image.

Thus, the present embodiment has been created focusing on the above-described circumstance. In the medical observation system 1 according to the present embodiment, a control device 20-1 provides a lens movement parameter that is common to left and right focus adjusting lenses to an endoscope device 10-1, and the parameter is specified on the basis of a focus evaluation value corresponding to a reference lens selected through an input of a user. The endoscope device 10-1 can adjust focus with respect to a camera that the user desires by moving left and right focus adjusting lenses on the basis of the lens movement parameter. According to the present embodiment, the user can comfortably perceive a stereoscopic image. Configurations of the endoscope device 10-1 and the control device 20-1 according to the present embodiment that achieve the above-described effect will be sequentially described in detail with reference to FIGS. 2 and 3.

1-2. Configuration of First Embodiment (Endoscope Device)

Figure 2:
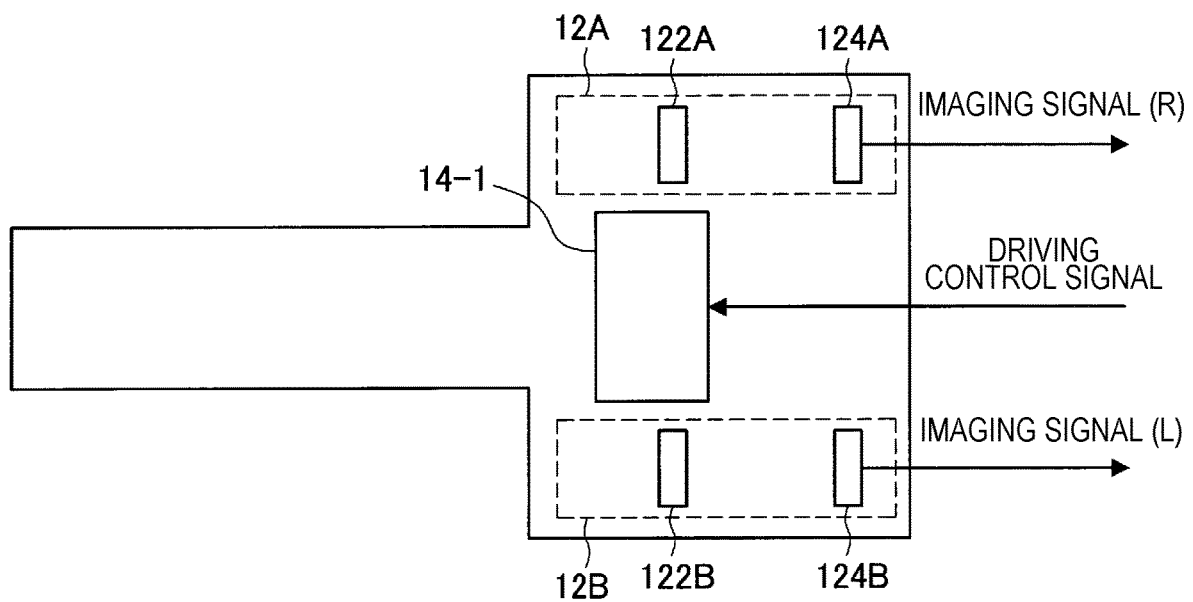
FIG. 2 is an illustrative diagram showing an internal configuration of an endoscope device 10-1 according to the embodiment.

FIG. 2 is an illustrative diagram schematically showing an internal configuration of the endoscope device 10-1 according to the present embodiment. The endoscope device 10-1 includes left-eye and right-eye cameras 12A and 12B, and a lens driving unit 14-1, as shown in FIG. 2.

The cameras 12A and 12B are camera modules for acquiring images. The cameras 12A and 12B include focus adjusting lenses 122A and 122B and image sensors 124A and 124B, respectively, as shown in FIG. 2. The focus adjusting lenses 122A and 122B are moved by the lens driving unit 14-1 to be used for focus adjustment (focusing) of the cameras 12A and 12B. The camera 12A performs imaging (converts light into an electric imaging signal) for a right eye and the image sensor 124A outputs a right-eye imaging signal (R). In addition, the camera 12B performs imaging for a left eye and the image sensor 124B outputs a left-eye imaging signal (L). Each of the output imaging signals is input to the control device 20-1, which will be described below.

The lens driving unit 14-1 is a unit for moving the focus adjusting lenses 122A and 122B of the cameras 12A and 12B, and is configured with, for example, a motor. The lens driving unit 14-1 is controlled in accordance with a driving control signal input from the control device 20-1, which will be described below, and moves the focus adjusting lenses 122A and 122B on the basis of a lens movement parameter included in a signal that is common to the focus adjusting lenses 122A and 122B.

An effect in which the endoscope device 10-1 can be realized in a smaller size is obtained by providing the lens driving unit 14-1, which is a lens driving control mechanism that is common to the cameras 12A and 12B, instead of designing each of the cameras 12A and 12B to have a lens driving unit.

(Control Device)

Figure 3:
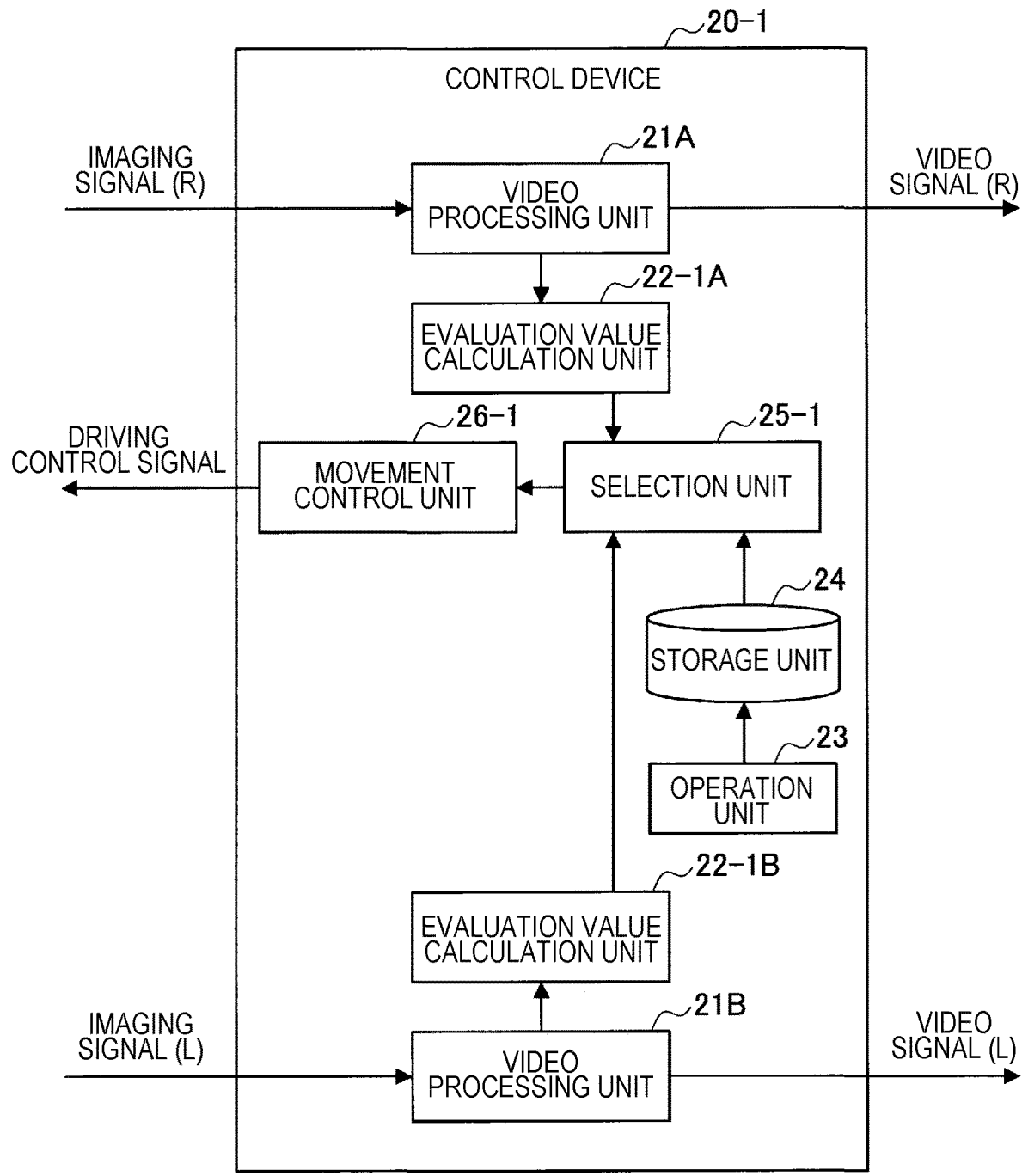
FIG. 3 is an illustrative diagram showing a configuration of a control device 20-1 according to the embodiment.

FIG. 3 is an illustrative diagram showing a configuration of the control device 20-1 (a lens driving control device) according to the present embodiment. The control device 20-1 is an information processing device having video processing units 21A and 21B, evaluation value calculation units 22-1A and 22-1B, an operation unit 23, a storage unit 24, a selection unit 25-1, and a movement control unit 26-1, as shown in FIG. 3.

Each of the video processing units 21A and 21B converts the imaging signal input from the cameras 12A and 12B into a video signal with which the display device 30 can perform display. For example, the video processing unit 21A converts the right-eye imaging signal (R) into a right-eye video signal (R), and the video processing unit 21B converts the left-eye imaging signal (L) into a left-eye video signal (L). In addition, the video processing units 21A and 21B provide images acquired from the imaging signals to the evaluation value calculation units 22-1A and 22-1B, respectively.

The evaluation value calculation units 22-1A and 22-1B calculate focus evaluation values indicating focus states of lenses for the respective focus adjusting lenses 122A and 122B and provide the values to the selection unit 25-1. Types and calculation methods of the focus evaluation values are different depending on AF systems used by the medical observation system 1.

An AF system used by the medical observation system 1 may be, for example, a contrast detection AF system in which contrast of an image obtained during imaging is evaluated and focus adjustment is performed on the basis of the evaluation to heighten the contrast. In this case, the evaluation value calculation units 22-1A and 22-1B may calculate focus evaluation values on the basis of contrast values of the images.

Furthermore, the AF system used by the medical observation system 1 may be a phase difference detection AF system in which light incoming from a lens is divided into two light images, a state of a deviation of focus is evaluated from a deviation of the images, and then focus adjustment is performed on the basis of the evaluation. In such a case, the image sensor for image acquisition included in the endoscope device 10-1 may be, for example, an image-plane phase-difference detecting image sensor having phase-difference pixels which divides light incoming from a lens into two light images and detects them. In addition, in this case, the evaluation value calculation units 22-1A and 22-1B may measure an interval between the two divided images and calculate focus evaluation values on the basis of the interval.

The operation unit 23 receives an input of a user with respect to a selection of one reference lens between the focus adjusting lenses 122A and 122B, which will be a reference in focus adjustment. The user may perform an input to set, for example, a lens corresponding to his or her dominant eye as a reference lens or a lens corresponding to his or her eye having high visual acuity between his or her left and right eyes as the reference lens. The user can select the reference lens using the operation unit 23 which can help him or her perceive stereoscopic images more comfortably.

The storage unit 24 stores selection information regarding the selection of the reference lens input by the user via the operation unit 23. The selection information that the storage unit 24 stores is provided to the selection unit 25-1, which will be described below. Since the storage unit 24 stores the selection information and provides the information to the selection unit 25-1, which will be described below, it is possible for the user to save his or her effort to perform selection to use the medical observation system 1 for the second time and thereafter, for example, when the same user consecutively uses the medical observation system 1 a plurality of times.

The selection unit 25-1 reads the selection information regarding the selection of the reference lens from the storage unit 24 and selects one reference lens from the focus adjusting lenses 122A and 122B. In addition, the selection unit 25-1 receives the focus evaluation values from the evaluation value calculation units 22-1A and 22-1B and provides a focus evaluation value corresponding to the selected reference lens to the movement control unit 26-1.

Since the reference lens is dynamically selected by the selection unit 25-1 in the present embodiment instead of being pre-set in a design or manufacturing stage, the selection is made, for example, in accordance with the dominant eye of the user, and thus the user can perceive stereoscopic image more comfortably.

The movement control unit 26-1 specifies a lens movement parameter that is common to the focus adjusting lenses 122A and 122B on the basis of the focus evaluation value corresponding to the reference lens selected by the selection unit 25-1. Here, the movement control unit 26-1 may receive only the focus evaluation value corresponding to the reference lens among the focus evaluation values from the selection unit 25-1 and specify the lens movement parameter without using the focus evaluation value corresponding to the lens other than the reference lens.

Methods for specifying a lens movement parameter by the movement control unit 26-1 differ depending on AF systems used by the medical observation system 1. For example, the movement control unit 26-1 may have a map on which a relation between a focus evaluation value and a suitable amount of lens movement for an AF system is defined in advance and calculate a lens movement parameter with reference to the map.

Further, the movement control unit 26-1 generates a driving control signal including information of the specified lens movement parameter and outputs the signal to the endoscope device 10-1.

1-3. Operation of First Embodiment

Figure 4:
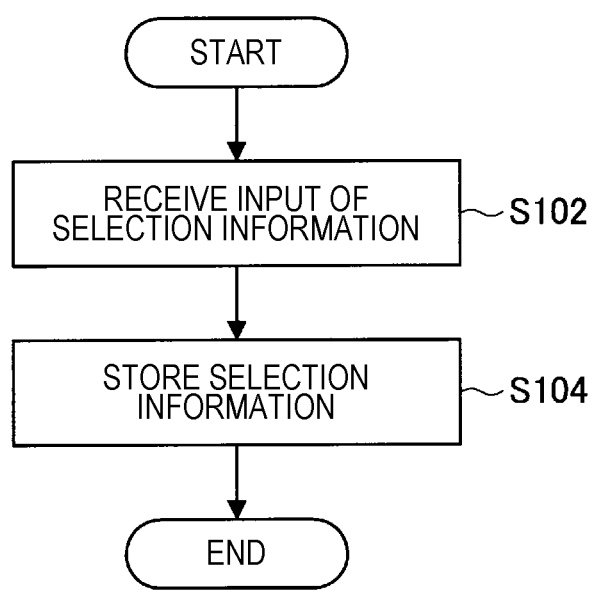
FIG. 4 is a flowchart for describing an operation of the medical observation system 1 according to the embodiment.
Figure 5:
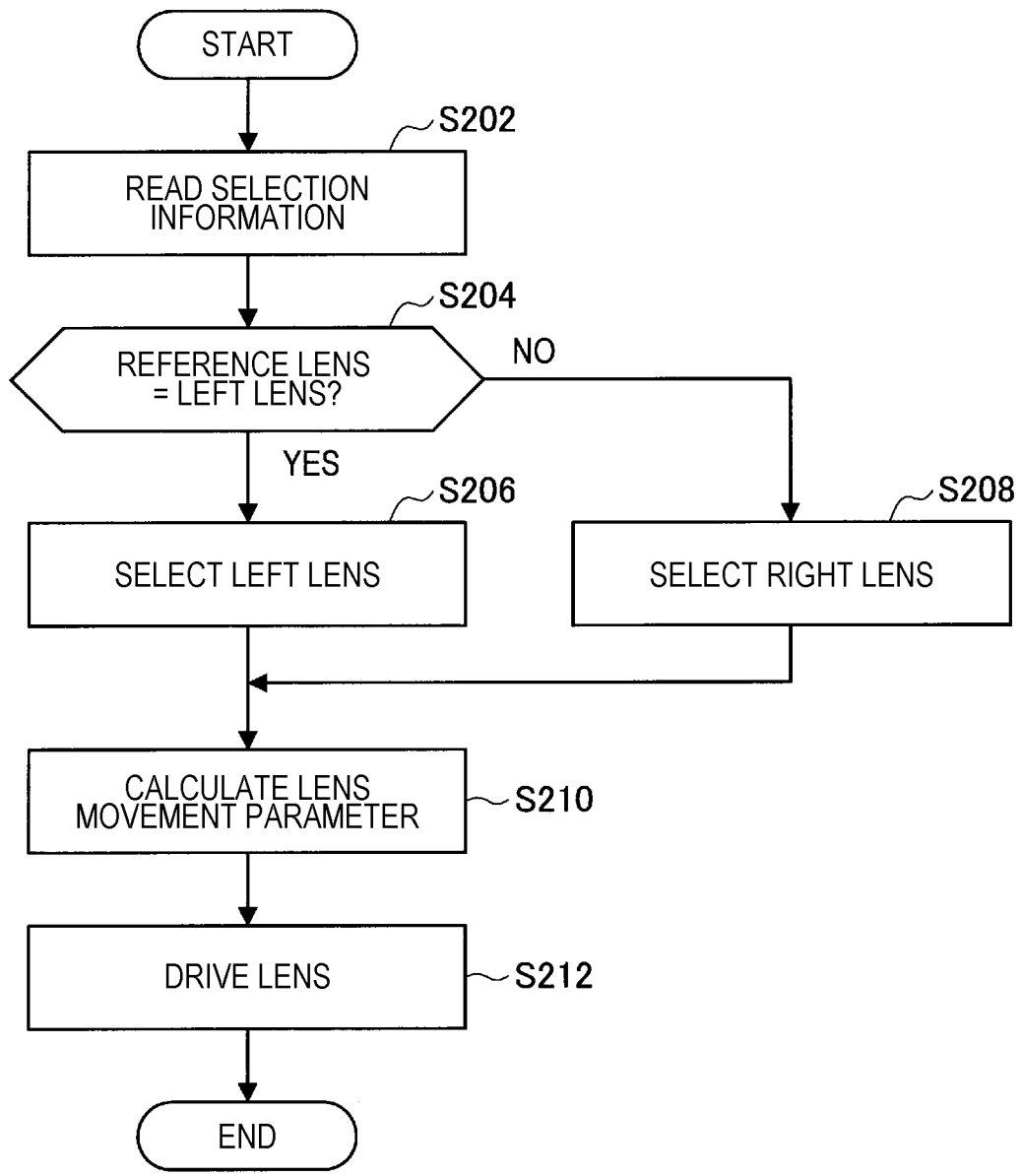
FIG. 5 is a flowchart for describing another operation of the medical observation system 1 according to the embodiment.

The examples of the configurations of the endoscope device 10-1 and the control device 20-1 included in the medical observation system 1 according to the first embodiment of the present disclosure have been described above. Next, examples of operations of the medical observation system 1 according to the present embodiment will be described with reference to FIGS. 4 and 5. FIGS. 4 and 5 are flowcharts for describing examples of the operations of the medical observation system 1 according to the present embodiment. The medical observation system 1 according to the present embodiment performs a selection information setting process shown in FIG. 4 and a lens driving control process shown in FIG. 5. The selection information setting process and the lens driving control process will be sequentially described in more detail below with reference to FIGS. 4 and 5.

(Selection Information Setting Process)

In the selection information setting process, first, the operation unit 23 receives an input of a user with respect to a selection of a reference lens, as shown in FIG. 4 (S102). The user may select and input, for example, his or her dominant eye between left and the right eyes. Next, the storage unit 24 receives selection information regarding the selection of the reference lens input by the user from the operation unit 23 and store the information (S104). When the storage unit 24 has already stored the selection information before Step S104, the selection information stored in the storage unit 24 is updated with the new selection information that the storage unit 24 received from the operation unit 23 in Step S104.

The above-described selection information setting process may be performed, for example, before the user uses the medical observation system 1 or when the user wants to change the reference lens while observing a body cavity of the patient 4 using the medical observation system 1.

(Lens Driving Control Process)

In the lens driving control process, first, the selection unit 25-1 reads selection information regarding the selection of the reference lens from the storage unit 24, as shown in FIG. 5 (S202). When the reference lens is the left lens (the focus adjusting lens 122B) (Yes in S204), the selection unit 25-1 receives (selects) a focus evaluation value corresponding to the left lens from the evaluation value calculation unit 22-1B and provides the value to the movement control unit 26-1 (S206). On the other hand, when the reference lens is the right lens (the focus adjusting lens 122A) (No in S204), the selection unit 25-1 receives (selects) a focus evaluation value corresponding to the right lens from the evaluation value calculation unit 22-1A and provides the value to the movement control unit 26-1 (S208).

Next, the movement control unit 26-1 calculates a lens movement parameter that is common to the focus adjusting lenses 122A and 122B on the basis of the focus evaluation value corresponding to the reference lens received from the selection unit 25-1 as described above (S210). The calculated lens movement parameter is included in a driving control signal and output from the movement control unit 26-1 to the endoscope device 10-1.

The lens driving unit 14-1 of the endoscope device 10-1 that received the driving control signal moves the focus adjusting lenses 122A and 122B on the basis of the lens movement parameter included in the driving control signal (S212).

The above-described lens driving control process may be repeated. For example, the lens driving control process may be repeated until the lens movement parameter that is common to the focus adjusting lenses 122A and 122B is equal to or lower than a predetermined threshold value. In addition, in that case, the operation unit 23 may have a function of rejecting an input of the user during a period in which the lens driving control process is repeated so that the selection information from the selection information setting process described with reference to FIG. 4 is not updated during the period.

1-4. Effect of First Embodiment

The endoscope device 10-1 and the control device 20-1 according to the first embodiment have been described above in detail. According to the present embodiment, the control device 20-1 provides the lens movement parameter that is common to the left and right focus adjusting lenses specified on the basis on the focus evaluation value corresponding to the reference lens that is selected on the basis of an input of the user to the endoscope device 10-1. The endoscope device 10-1 can acquire a stereoscopic image that the user can comfortably perceive by moving the left and right focus adjusting lenses on the basis of the lens movement parameter.

1-5. Modified Examples of First Embodiment

The first embodiment of the present disclosure has been described above. Several modified examples of the present embodiment will be described. Note that the modified examples to be described below may be applied to the present embodiment alone or as a combination. In addition, each of the modified examples may be applied in place of or in addition to the configuration described in the present embodiment.

Modified Example 1

Although the example in which the storage unit 24 stores one piece of selection information and, when the user inputs new selection information via the operation unit 23, the selection information stored in the storage unit 24 is updated with the new input selection information has been described above, the present technology is not limited thereto.

Figure 6:
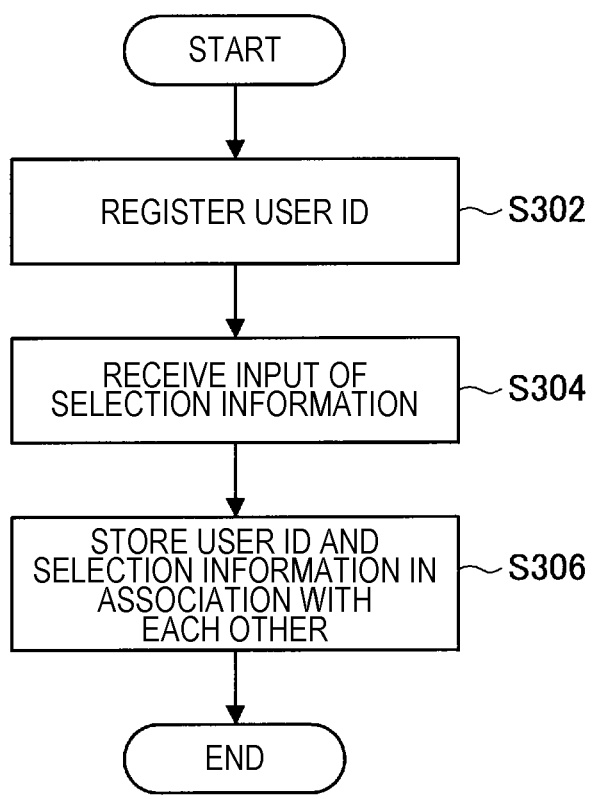
FIG. 6 is a flowchart for describing an operation of a modified example according to the embodiment.

For example, the storage unit 24 may store selection information for each user in association with user information (a user ID) of the user. FIG. 6 is a flowchart for describing a selection information setting process when the storage unit 24 stores selection information for each user in association with a user ID of the user.

First, the operation unit 23 receives an input of a user with respect to a user ID and the input user ID is stored (registered) in the storage unit 24 (S302). Next, the operation unit 23 receives an input of selection information (S304) and the storage unit 24 stores the input selection information and the user ID in association with each other (S306).

The above-described selection information setting process for each user may be repeated the same number of times as the number of users who are using the medical observation system 1. FIG. 7 is a table showing an example of an association table of user IDs and selection information stored in the storage unit 24 after the selection information setting process is repeated. The storage unit 24 stores one piece of selection information for each user ID in the present modified example, as shown in FIG. 7. That is, the storage unit 24 stores the same number of pieces of selection information as the number of user IDs when there are a plurality of user IDs.

According to this configuration, when the medical observation system 1 has a user authentication function, for example, a user with a user ID stored in association with selection information who has been authenticated therewith can save effort to select a reference lens.

Modified Example 2

Although the example in which the movement control unit 26-1 receives only the focus evaluation value corresponding to the reference lens from the selection unit 25-1 and specifies the lens movement parameter without using the focus evaluation value corresponding to the lens other than the reference lens has been described above, the present technology is not limited thereto.

For example, the movement control unit 26-1 may specify a lens movement parameter that is common to the focus adjusting lenses 122A and 122B on the basis of both the focus evaluation value corresponding to the reference lens (a reference evaluation value) and the focus evaluation value corresponding to the lens other than the reference lens (a non-reference evaluation value).

For example, the movement control unit 26-1 may specify an average value of lens movement parameters specified on the basis of the focus evaluation values calculated for the focus adjusting lenses 122A and 122B as the lens movement parameter that is common to the focus adjusting lenses 122A and 122B. Note that, since the movement control unit 26-1 does not use the selection information of the reference lens in this case, the control device may not have the operation unit, storage unit, and selection unit. According to this configuration, since a lens movement parameter that helps the same degree of focus be obtained for both the lens corresponding to the left eye and the lens corresponding to the right eye can be specified, images with the same quality can be presented to both eyes. It is know that, if a human being visually senses different degrees of quality of presented images with his or her left and right eyes, he or she perceives a deteriorated feeling of depth or deteriorated quality of a stereoscopic image, however, such deterioration in a feeling of depth or quality of a stereoscopic image can be reduced by presenting images with the same degree of quality to both eyes as described above.

Furthermore, the movement control unit 26-1 may specify, as a common lens movement parameter, a parameter acquired from a weighted average of the lens movement parameter, which is specified on the basis of the reference evaluation value, and the lens movement parameter, which is specified on the basis of the non-reference evaluation value. In particular, the movement control unit 26-1 may acquire the weighted average by setting a weight of the lens movement parameter specified on the basis of the reference evaluation value to be greater than a weight of the lens movement parameter specified on the basis of the non-reference evaluation value. According to this configuration, a lens movement parameter, with which the reference lens gains more accurate focus than the lens other than the reference lens and a focus state of the lens other than the reference lens is also reflected in accordance with the weight, can be specified.

Modified Example 3

Although the example in which the evaluation value calculation units 22-1A and 22-1B calculate the respective focus evaluation values and either of the focus evaluation values is provided to the movement control unit 26-1 depending on the reference lens selected by the selection unit 25-1 has been described above, the present technology is not limited thereto.

For example, only the focus evaluation value corresponding to the reference lens selected by the selection unit 25-1 may be calculated. In addition, the lens movement parameters may be specified on the basis of focus evaluation values corresponding to the respective lenses and the lens movement parameter corresponding to the reference lens selected by the selection unit 25-1 may be included in the driving control signal and provided to the endoscope device 10-1.

Modified Example 4

Although the example in which the reference lens is selected on the basis of an input of the user has been described above, the present technology is not limited thereto. For example, the selection unit 25-1 may select the reference lens on the basis of images acquired by the cameras 12A and 12B.

For example, the selection unit 25-1 may recognize a subject in two images acquired by the cameras 12A and 12B, specify a position of the subject in the two images, and select the reference lens in accordance with the position of the subject. When the position of the subject is located on the right side (for example, in a right half) of either or both of the two images, the selection unit 25-1 may select the focus adjusting lens 122A of the camera 12A which performs right-eye imaging as the reference lens. In addition, when the position of the subject is located on the left side (e.g., a left half) of either or both of the two images, the selection unit 25-1 may select the focus adjusting lens 122B of the camera 12B which performs left-eye imaging as the reference lens.

Further, the selection unit 25-1 may recognize a subject in the two images acquired by the cameras 12A and 12B, specify a size of the subject in the two images, and select the reference lens in accordance with the size of the subject. When a size of the subject in the image acquired by the camera 12A is greater than a size of the subject in the image acquired by the camera 12B, the selection unit 25-1 may select the focus adjusting lens 122A of the camera 12A as the reference lens. In addition, when the size of the subject in the image acquired by the camera 12B is greater than the size of the subject in the image acquired by the camera 12A, the selection unit 25-1 may select the focus adjusting lens 122B of the camera 12B as the reference lens.

According to this configuration, the reference lens can be automatically selected in consideration of a subject, and thus a user can save his or her effort to select the reference lens.

2. Second Embodiment 2-1. Overview of Second Embodiment

In the above-described first embodiment, the control device outputs a lens movement parameter that is common to the left and right focus adjusting lenses, and the endoscope device moves the left and right focus adjusting lenses on the basis of the lens movement parameter that is common to both of the lenses. In contrast, a case in which an endoscope device moves left and right focus adjusting lenses individually will be described as a second embodiment.

When the endoscope device moves the left and right focus adjusting lenses individually, a medical observation system thereof has a different characteristic from the case in which the left and right focus adjusting lenses are moved on the basis of the lens movement parameter that is common to the lenses described in the first embodiment above. Thus, as a comparative example of the second embodiment, a case in which a control device independently calculates lens movement parameters for the left and right focus adjusting lenses and an endoscope device moves the left and right focus adjusting lenses individually will be described with reference to FIGS. 8 and 9.

Configuration of Comparative Example

Figure 8:
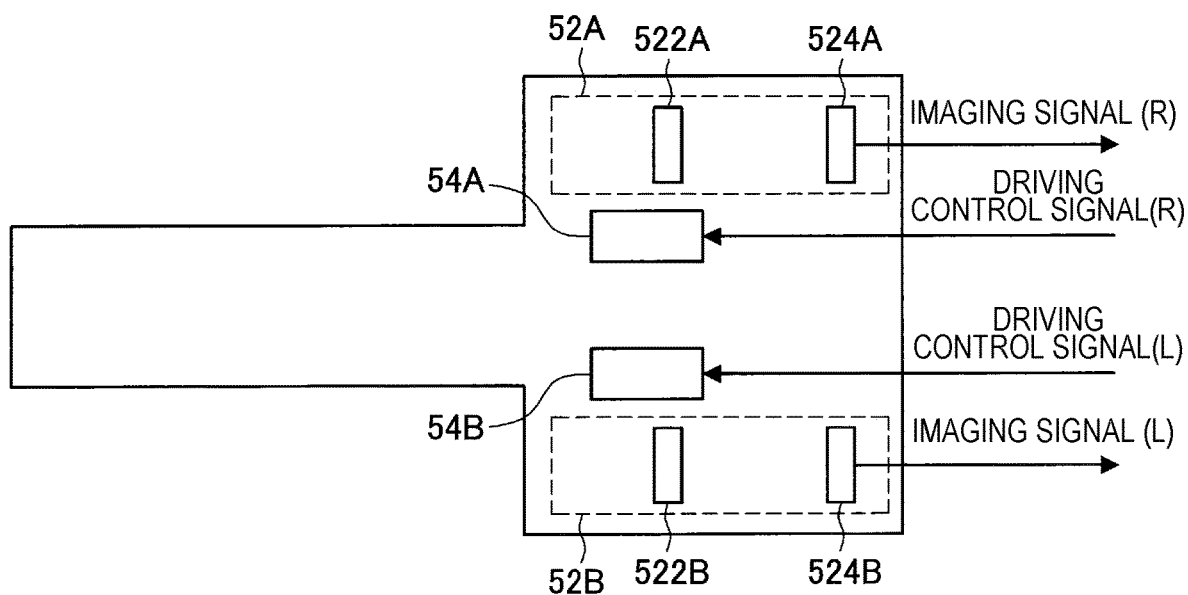
FIG. 8 is an illustrative diagram showing an internal configuration of an endoscope device 50 according to a comparative example of a second embodiment of the present disclosure.

FIG. 8 is an illustrative diagram schematically showing an internal configuration of an endoscope device 50 according to the comparative example of the second embodiment. The endoscope device 50 includes left-eye and right-eye cameras 52A and 52B and lens driving units 54A and 54B, as shown in FIG. 8.

The cameras 52A and 52B, like the cameras 12A and 12B according to the first embodiment, are camera modules including focus adjusting lenses 522A and 522B and image sensors 524A and 524B, as shown in FIG. 8. In addition, since configurations of the focus adjusting lenses 522A and 522B and the image sensors 524A and 524B are substantially the same as those of the focus adjusting lenses 122A and 122B and the image sensors 124A and 124B according to the first embodiment, descriptions thereof will be omitted here.

The lens driving units 54A and 54B are units for moving the respective focus adjusting lenses 522A and 522B of the cameras 52A and 52B, and are configured with, for example, motors. The lens driving unit 54A is controlled with a right-eye driving control signal (R) input from a control device 60, which will be described below, to move the focus adjusting lens 522A on the basis of a right-eye lens movement parameter included in the signal. Likewise, the lens driving unit 54B is controlled with a left-eye driving control signal (L) input from the control device 60, which will be described below, to move the focus adjusting lens 522B on the basis of a left-eye lens movement parameter included in the signal.

Figure 9:
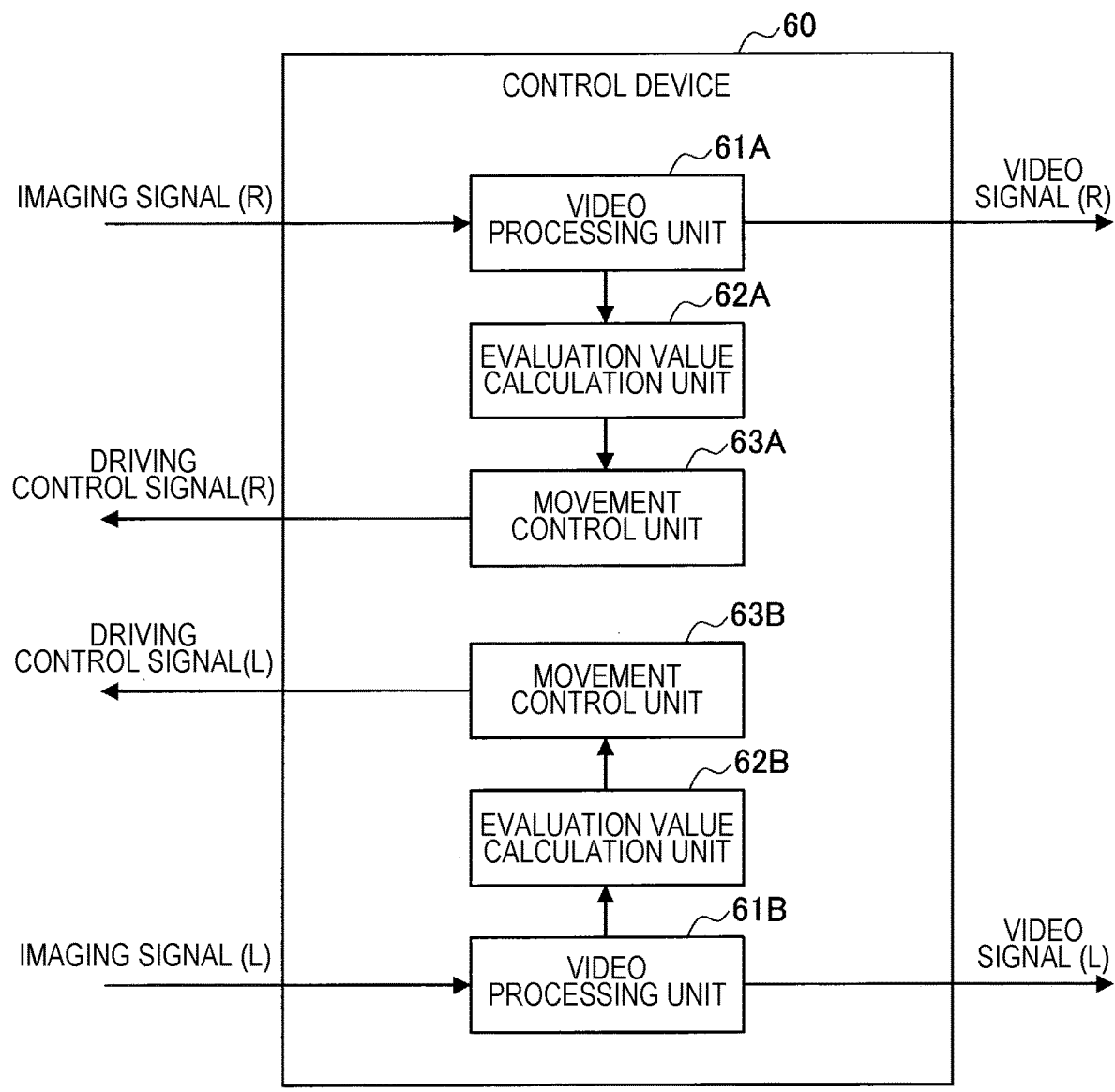
FIG. 9 is an illustrative diagram showing a configuration of a control device 60 according to the comparative example.

FIG. 9 is an illustrative diagram showing a configuration of the control device 60 according to the comparative example of the second embodiment. The control device 60 is an information processing device having video processing units 61A and 61B, evaluation value calculation units 62A and 62B, and movement control units 63A and 63B, as shown in FIG. 9. Since configurations of the video processing units 61A and 61B and the evaluation value calculation units 62A and 62B are substantially the same as those of the video processing units 21A and 21B and the evaluation value calculation units 22-1A and 22-1B according to the first embodiment, description thereof will be omitted here.
[0069]

The movement control units 63A and 63B respectively specify lens movement parameters corresponding to the focus adjusting lenses 522A and 522B on the basis of focus evaluation values calculated by the evaluation value calculation units 62A and 62B. A method for specifying the lens movement parameters from the focus evaluation values is similar to the specification method used by the movement control unit 26-1 described in the first embodiment. In addition, the movement control unit 63A outputs the right-eye driving control signal (R) including the lens movement parameter corresponding to the focus adjusting lens 522A to the endoscope device 50. Likewise, the movement control unit 63B outputs the left-eye driving control signal (L) including the lens movement parameter corresponding to the focus adjusting lens 522B to the endoscope device 50.

AF Control According to Comparative Example

Configurations of the endoscope device 50 and the control device 60 according to the present comparative example have been described above. In the present comparative example, the focus evaluation values and the lens movement parameters corresponding to the focus adjusting lenses 522A and 522B are calculated and specified independently as described above. Thus, accurate focus adjustment (focusing) can be performed for each of the cameras 52A and 52B.

However, when images acquired by the cameras 52A and 52B are displayed on a display device via the control device 60, stereoscopic images that are difficult for a user to comfortably perceive may be displayed. Thus, characteristics of images acquired by the cameras 52A and 52B as a result of AF control according to the present comparative example will be described below with reference to FIGS. 10 and 11.

Figure 10:
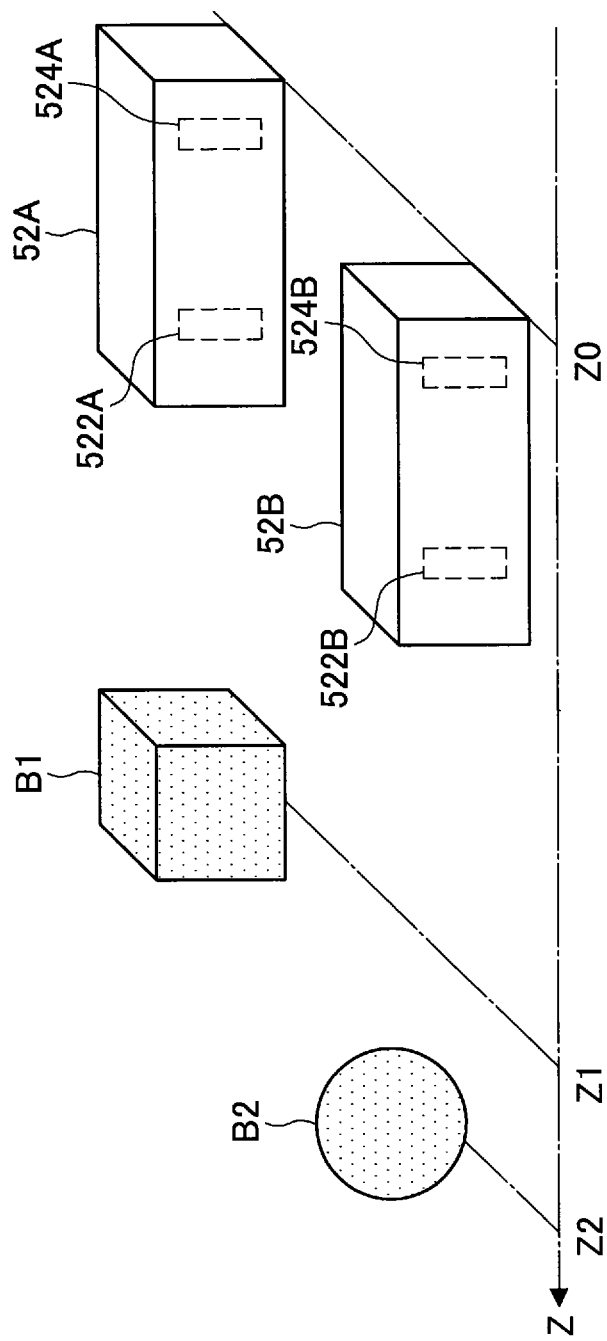
FIG. 10 is an illustrative diagram for describing lens control according to a relevant technology.

FIG. 10 is an illustrative diagram showing an example of a photographing situation of the cameras 52A and 52B. Although the cameras 52A and 52B are inherently present in the endoscope device 50 as described with reference to FIG. 8, the cameras 52A and 52B are schematically shown as independent cameras in FIG. 10.

The camera 52A (a right camera) and the camera 52B (a left camera) are disposed to the left and right, as shown in FIG. 10 to photograph objects B1 and B2. Comparing positions of elements on a Z axis with each other, the left and right cameras are located at a position Z0, the object B1 at a position Z1, and the object B2 at a position Z2, as shown in FIG. 10. In addition, a distance between the position Z0 and the position Z1 is shorter than a distance between the position Z0 and the position Z2.

Figure 11:
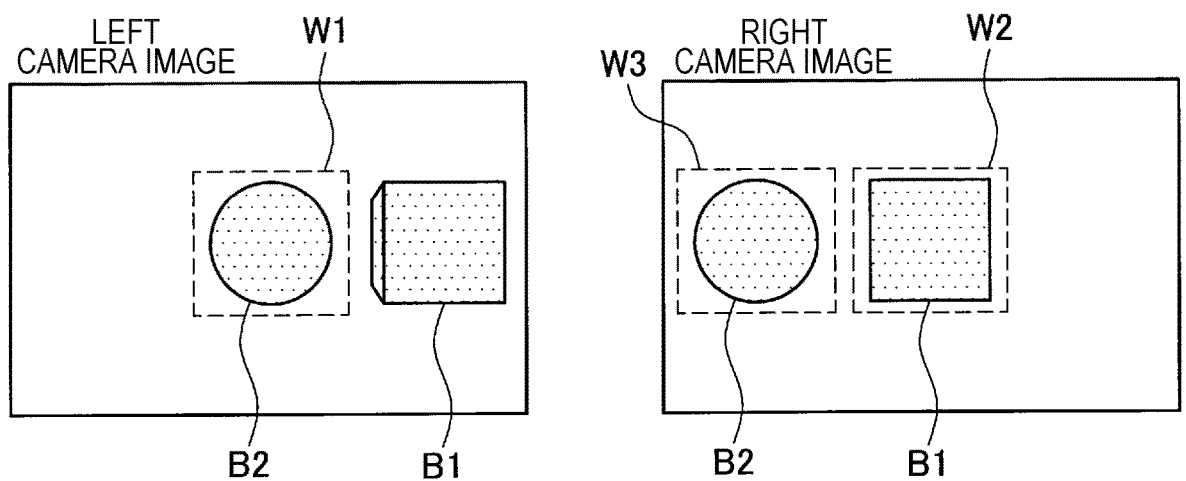
FIG. 11 is an illustrative diagram for describing lens control according to a relevant technology.

FIG. 11 is an illustrative diagram showing an example of images acquired by the left and right cameras in the photographing situation shown in FIG. 10. In a left camera image acquired by the left camera (the camera 52B), the object B2 is captured at the center of the image and the object B1 is captured at the right side of the image, as shown in FIG. 11. In addition, in a right camera image acquired by the right camera (the camera 52A), the object B1 is captured at the center of the image and the object B2 is captured at the left side of the image, as shown in FIG. 11.

Here, there is a case during the AF control of the cameras in which focus is adjusted, for example, to be on subjects projected near the center of a screen. That is, the left camera adjusts focus to be on a subject (the object B2 in the example of FIG. 11) included within an evaluation frame W1. In addition, the right camera adjusts focus to be on a subject (the object B1 in the example of FIG. 11) included within an evaluation frame W2.

Here, if a display device displays the above-described left camera image and right camera image shown in FIG. 11 as a left-eye image and a right-eye image, the objects that are focused on differently on the left and right are presented. As a result, there is concern of the different focusing hindering the user from comfortably perceiving stereoscopic images.

Thus, the present embodiment has been created focusing on the above-described circumstance. In a medical observation system 1 according to the present embodiment, a control device 20-2 sets a method for calculating a focus evaluation value corresponding to a lens other than a reference lens on the basis of a focus evaluation value corresponding to the reference lens, and provides calculated lens movement parameters of the lenses to an endoscope device 10-2. The endoscope device 10-2 can adjust focus so that left and right cameras focus on a subject by moving left and right focus adjusting lenses individually on the basis of the lens movement parameters. According to the present embodiment, a user can comfortably perceive stereoscopic images since the left and right cameras focus on the same subject. Configurations of the endoscope device 10-2 and the control device 20-2 according to the present embodiment that exhibit the effect will be sequentially described below with reference to FIGS. 12 and 13.

2-2. Configuration of Second Embodiment

The medical observation system 1, like the medical observation system 1 according to the first embodiment described with reference to FIG. 1, according to the second embodiment includes the endoscope device 10-2, the control device 20-2, and a display device 30.

(Endoscope Device)

Figure 12:
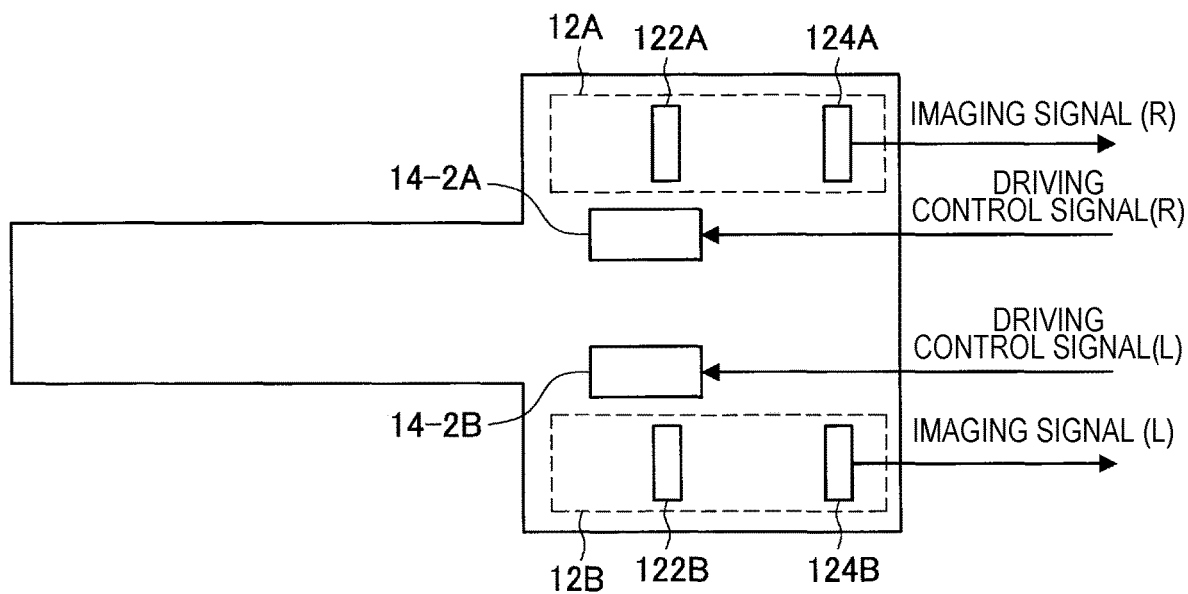
FIG. 12 is an illustrative diagram showing an internal configuration of an endoscope device 10 according to the second embodiment of the present disclosure.

FIG. 12 is an illustrative diagram schematically showing an internal configuration of the endoscope device 10-2 according to the present embodiment. The endoscope device 10-2 has left-eye and right-eye cameras 12A and 12B and lens driving units 14-2A and 14-2B, as shown in FIG. 12. Since configurations of the cameras 12A and 12B shown in FIG. 12 are substantially the same as those of the cameras 12A and 12B according to the first embodiment described with reference to FIG. 2, description thereof will be omitted here. In addition, since configurations of the lens driving units 14-2A and 14-2B shown in FIG. 12 are substantially the same as those of the lens driving units 54A and 54B according to the comparative example of the present embodiment described with reference to FIG. 8, descriptions thereof will be omitted here.

Figure 13:
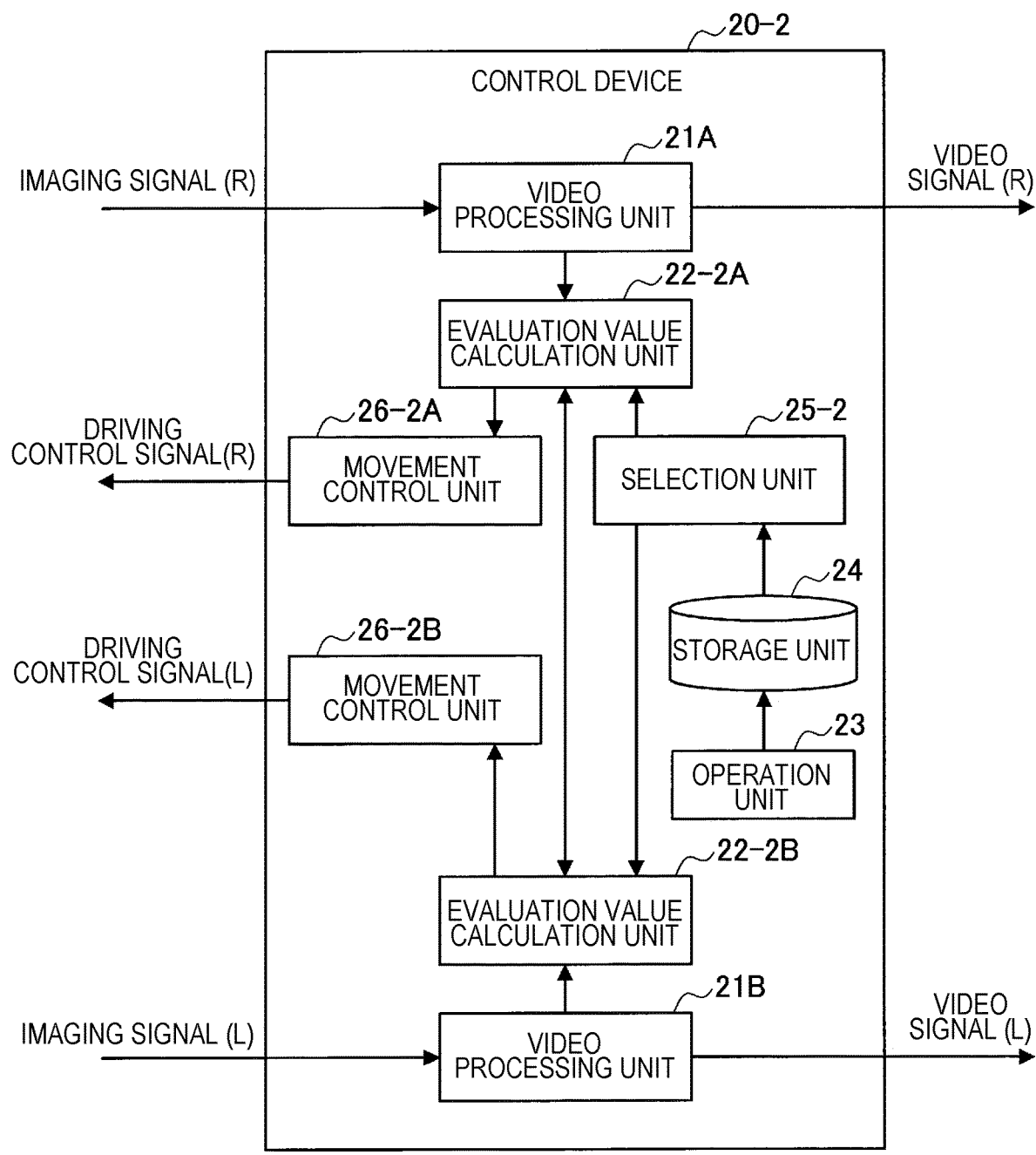
FIG. 13 is an illustrative diagram showing an internal configuration of a control device 20 according to the embodiment.

FIG. 13 is an illustrative diagram showing a configuration of the control device 20-2 (lens driving control device) according to the present embodiment. The control device 20-2 is an information processing device having video processing units 21A and 21B, evaluation value calculation units 22-2A and 22-2B, an operation unit 23, a storage unit 24, a selection unit 25-2, and movement control units 26-2A and 26-2B, as shown in FIG. 13.

Since configurations of the video processing units 21A and 21B, the operation unit 23, and the storage unit 24 are the same as those of the video processing units 21A and 21B, the operation unit 23, and the storage unit 24 according to the first embodiment described with reference to FIG. 3, description thereof will be omitted here.

The evaluation value calculation units 22-2A and 22-2B calculate focus evaluation values indicating focus states of lenses for the respective focus adjusting lenses 122A and 122B and provides the values to the movement control units 26-2. Note that the focus evaluation values according to the present embodiment may include information of evaluation frames (such as areas used to obtain the focus evaluation values) described with reference to FIG. 11.

In addition, the evaluation value calculation units 22-2A and 22-2B receive information of a reference lens selected by the selection unit 25-2 from the selection unit 25-2 and set a method for calculating a focus evaluation value corresponding to a lens other than the reference lens (a non-reference lens) on the basis of a focus evaluation value corresponding to the reference lens. For example, the evaluation value calculation units 22-2A and 22-2B may set the method for calculating the focus evaluation values by setting evaluation frames to be used to calculate the focus evaluation value corresponding to the non-reference lens on the basis of an evaluation frame used to calculate the focus evaluation value corresponding to the reference lens.

When the reference lens selected by the selection unit 25-2 is a focus adjusting lens 122B, for example, the evaluation value calculation unit 22-2B calculates the focus evaluation value corresponding to the reference lens (the focus adjusting lens 122B). Here, since the type of calculated focus evaluation value and the calculation method are similar to those of first embodiment, detailed description thereof will be omitted. In addition, at this time, the evaluation value calculation unit 22-2A receives the focus evaluation value corresponding to the reference lens from the evaluation value calculation unit 22-2B and sets an evaluation frame to be used to calculate a focus evaluation value corresponding to the focus adjusting lens 122A on the basis of the evaluation frame used to calculate the focus evaluation value. Furthermore, the evaluation value calculation unit 22-2A calculates the focus evaluation value corresponding to the focus adjusting lens 122A, which is the non-reference lens, using the evaluation frame.

Returning to FIG. 11, a specific example in which the evaluation value calculation units 22-2A and 22-2B calculate the focus evaluation values will be described. When the reference lens is the focus adjusting lens 122B, the evaluation value calculation unit 22-2B calculates the focus evaluation value corresponding to the focus adjusting lens 122B using the evaluation frame W1 near the center of the left camera image shown in FIG. 11. Further, the evaluation value calculation unit 22-2A receives the focus evaluation value corresponding to the reference lens from the evaluation value calculation unit 22-2B, sets an evaluation frame W3 to correspond to the evaluation frame W1, and calculates the focus evaluation value corresponding to the focus adjusting lens 122A using the evaluation frame W3. Note that the evaluation value calculation unit 22-2A may set the evaluation frame W3 to correspond to the evaluation frame W1 on the basis of, for example, information of a disposition of the cameras 12A and 12B acquired in advance, depth information obtained through stereo matching of the left and right camera images, and the like.

Focus of the left and right cameras is adjusted to be on the same subject (the object B2 in FIG. 11) by calculating the focus evaluation value corresponding to the non-reference lens using the evaluation frame corresponding to the evaluation frame used to calculate the focus evaluation value corresponding to the reference lens. If the left and right cameras capture images in the state in which focus is on the same subject, a user can comfortably perceive stereoscopic images.

The selection unit 25-2 reads selection information regarding a selection of the reference lens from the storage unit 24 and selects one reference lens from the focus adjusting lenses 122A and 122B. In addition, the selection unit 25-2 provides information of the selected reference lens to the evaluation value calculation units 22-2A and 22-2B.

The subject to be focused on by the left and right cameras is a subject projected near the center of an image corresponding to the reference lens on the basis of an input of the user in the present embodiment. Thus, when the user inputs a selection such that a focus adjusting lens corresponding to a dominant eye of the user serves as a reference lens, for example, the left and right cameras focus on a subject projected near the center of an image presented to the dominant eye of the user so that the user can comfortably perceive stereoscopic images. [0089]

The movement control units 26-2A and 26-2B specify lens movement parameters corresponding to the focus adjusting lenses 122A and 122B on the basis of the focus evaluation values calculated by the evaluation value calculation units 22-2A and 22-2B. A method for specifying the lens movement parameters from the focus evaluation values is similar to the specified method by the movement control unit 26-1 described in the first embodiment. In addition, the movement control unit 26-2A outputs a right-eye driving control signal (R) including the lens movement parameter corresponding to the focus adjusting lens 122A to the endoscope device 10-2. Likewise, the movement control unit 26-2B outputs a left-eye driving control signal (L) including the lens movement parameter corresponding to the focus adjusting lens 122B to the endoscope device 10-2.

2-3. Operation of Second Embodiment

Figure 14:
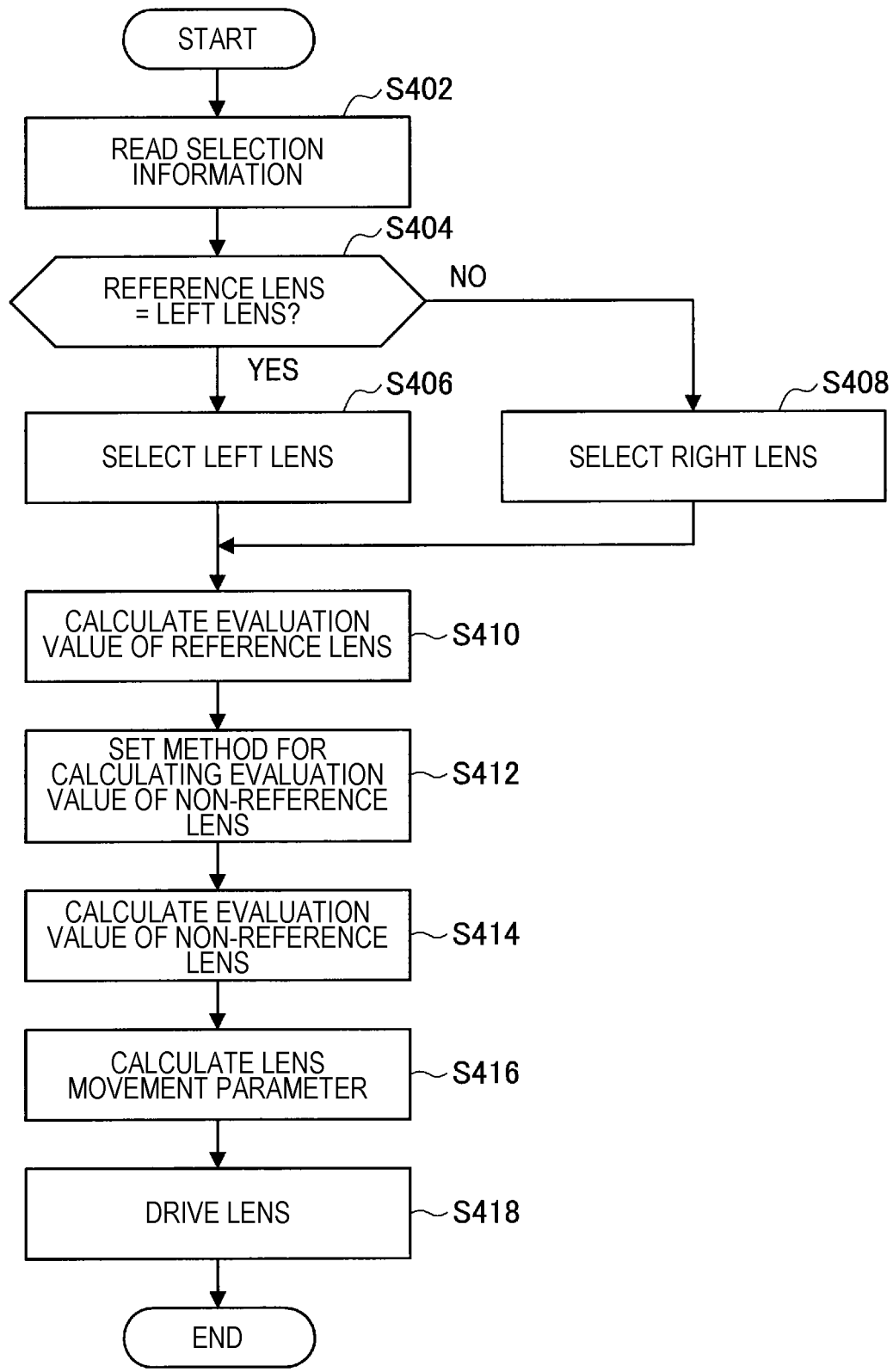
FIG. 14 is a flowchart for describing an operation of the embodiment.

The examples of the configurations of the endoscope device 10-2 and the control device 20-2 included in the medical observation system 1 according to the second embodiment of the present disclosure have been described above. Next, an example of an operation of the medical observation system 1 according to the present embodiment will be described with reference to FIG. 14. FIG. 14 is a flowchart for describing the example of the operation of the medical observation system 1 according to the present embodiment. The medical observation system 1 according to the present embodiment performs a lens driving control process shown in FIG. 14. In addition, although the medical observation system 1 according to the present embodiment performs a selection information setting process, and since this process is similar to the selection information setting process performed by the medical observation system 1 according to the first embodiment described with reference to FIG. 4, description thereof will be omitted. The lens driving control process will be described in detail with reference to FIG. 14.

First, the selection unit 25-2 reads selection information regarding a selection of the reference lens from the storage unit 24 as shown in FIG. 14 (S402). When the reference lens is the left lens (the focus adjusting lens 122B) (Yes in S404), the selection unit 25-2 selects the left lens as the reference lens and provides information of the selected reference lens to the evaluation value calculation units 22-2A and 22-2B (S406). On the other hand, when the reference lens is the right lens (the focus adjusting lens 122A) (No in S404), the selection unit 25-2 selects the right lens as the reference lens and provides information of the selected reference lens to the evaluation value calculation units 22-2A and 22-2B (S408).

Next, an evaluation value calculation unit corresponding to the reference lens among the evaluation value calculation units 22-2A and 22-2B calculates an evaluation value of the reference lens (S410). Further, the other evaluation value calculation unit (corresponding to a non-reference lens) sets an evaluation frame to be used to calculate the non-reference lens on the basis of an evaluation frame used to calculate the evaluation value of the reference lens (S412), and calculates a focus evaluation value corresponding to the non-reference lens (S414).

Then, the movement control units 26-2A and 26-2B receive the focus evaluation values from the evaluation value calculation units 22-2A and 22-2B to calculate lens movement parameters corresponding to the focus adjusting lenses 122A and 122B (S416). The calculated lens movement parameters are included in a driving control signal (R) and a driving control signal (L) and output from the movement control units 26-2A and 26-2B to the endoscope device 10-2.

The lens driving units 14-2A and 14-2B of the endoscope device 10-2 that received the driving control signal (R) and the driving control signal (L) move the focus adjusting lenses 122A and 122B on the basis of the lens movement parameters included in the driving control signals (S418).

This lens driving control process according to the above-described embodiment may be repeated like the lens driving control process according to the first embodiment.

2-4. Effect of Second Embodiment

The endoscope device 10-2 and the control device 20-2 according to the second embodiment have been described above in detail. According to the present embodiment, the control device 20-2 sets the method for calculating the focus evaluation value corresponding to the lens other than the reference lens on the basis of the focus evaluation value corresponding to the reference lens and provides the calculated lens movement parameters for the lenses to the endoscope device 10-2. The endoscope device 10-2 moves the left and right focus adjusting lenses individually on the basis of the lens movement parameters to perform focus adjustment so that the left and right cameras focus on the same subject, and thus the user can acquire stereoscopic images that he or she can comfortably perceive.

Note that the modified examples described in relation to the first embodiment can also be applied to the second embodiment.

3. Third Embodiment

3-1. Overview of Third Embodiment

In the medical observation system 1 shown in FIG. 1, the endoscope device 10 can be fixed with, for example, a hand of a person or the like. If the endoscope device 10 fixed with a hand of a person is moved (shakes) while a body cavity of a patient is observed using the medical observation system 1, camera shake occurs in a video acquired by the endoscope device 10. As a result, it is difficult for a user to comfortably observe a video displayed on the display device 30.

Electronic camera shake correction has been performed in order to correct captured images in the past as a method for reducing influence of the camera shake. The correction (reducing influence of camera shake) is performed by performing, for example, a projective transformation on a current image such that a difference between a past image and a current image is cancelled with reference to the past image.

However, there are cases in which image quality significantly deteriorates due to a projective transformation in electronic camera shake correction depending on camera shake that occurred. In particular, when quality of an image presented to a dominant eye of a user is deteriorated, there is concern that comfortable stereoscopic perception of the user is seriously hindered.

In addition, when two cameras are provided, as in the endoscope device 10, a user who observes a video is actually observing different videos with his or her left and right eyes, and thus he or she easily feels fatigue caused by camera shake more than when observing a video captured by one camera. Particularly when there are different amounts of camera shake between the cameras, a mismatch occurs in a vertical direction, which makes it difficult to perceive stereoscopic images and further increases a feeling of fatigue.

A difference in an amount of camera shake between two cameras (an L camera and an R camera) that are disposed to the left and right of an endoscope device will be described with reference to FIGS. 15 to 17. Note that, although the endoscope device inherently has two cameras therein, the L camera (left camera) and the R camera (right camera) will be schematically described as individual cameras below. It is assumed, however, that a relative disposition of the L camera and the R camera is fixed and the relative disposition (a positional relation) of the L camera and the R camera does not change even when each of the cameras moves due to vibration or the like.

Figure 15:
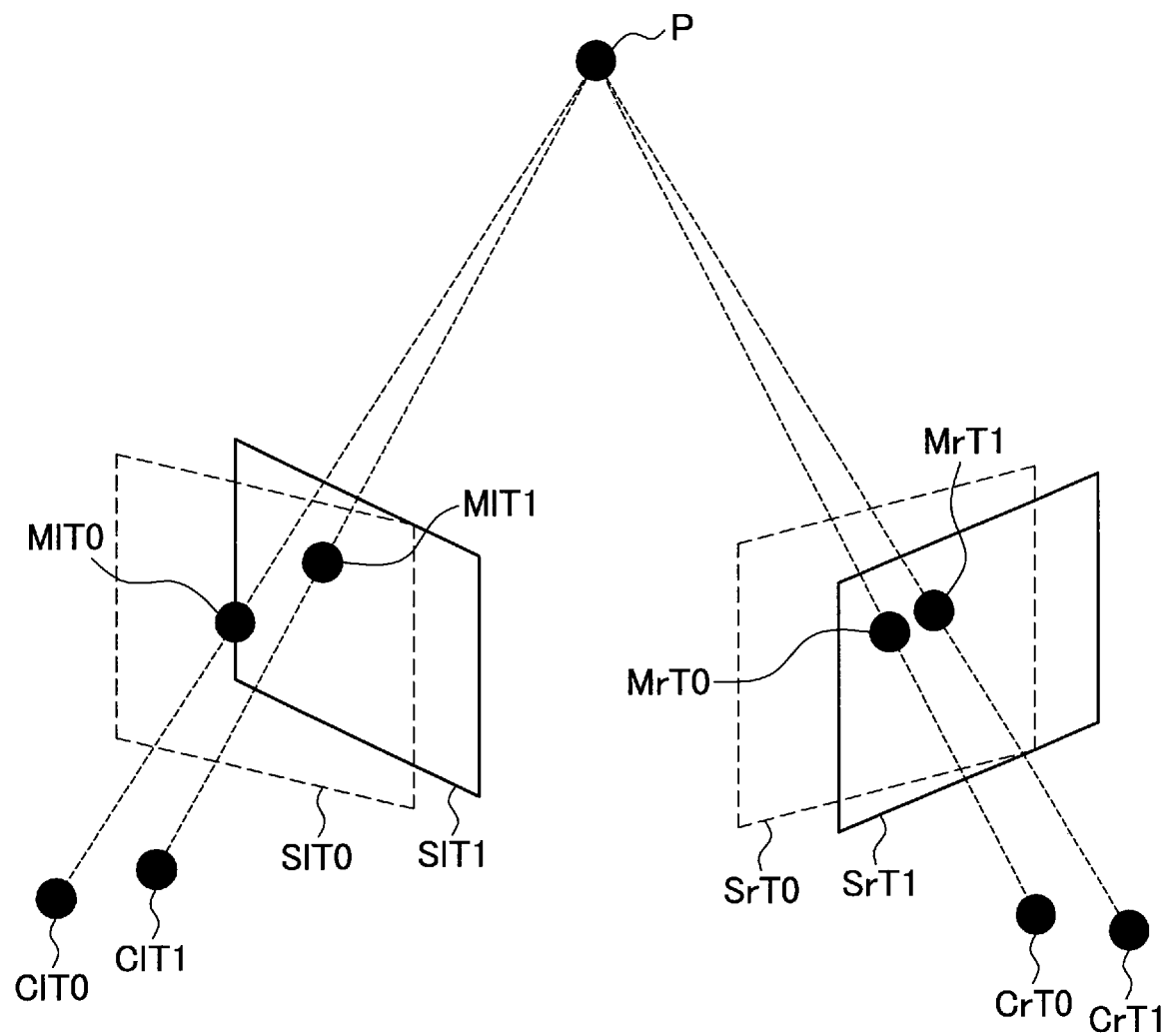
FIG. 15 is an illustrative diagram for describing an overview of camera shake correction according to a third embodiment of the present disclosure.
Figure 16:
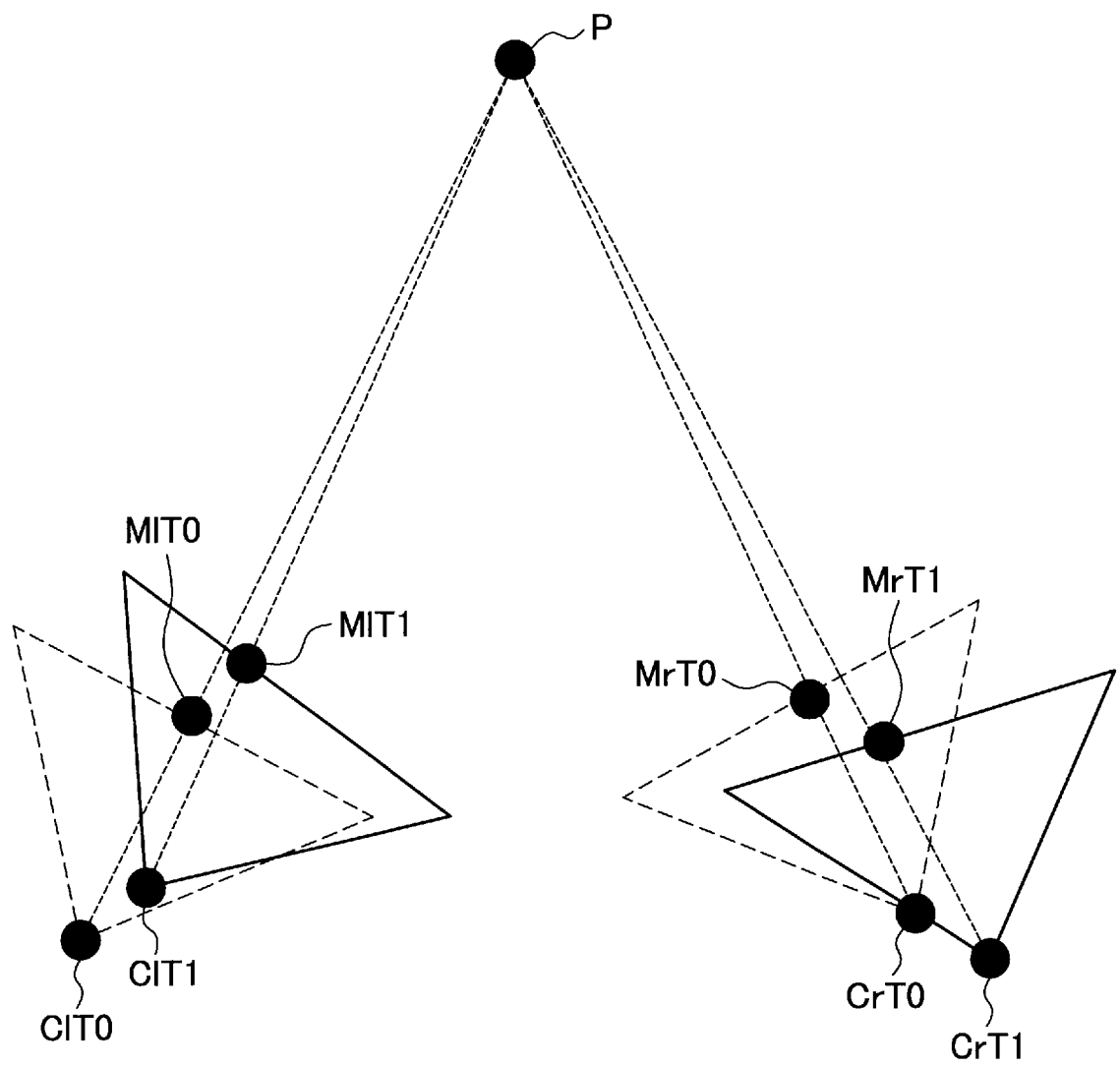
FIG. 16 is an illustrative diagram for describing the overview of camera shake correction according to the embodiment.

FIGS. 15 to 17 are illustrative diagrams for describing camera shake occurring in the L camera and the R camera from a time T0 to a time T1. FIG. 15 is a schematic diagram viewed from a rear side of the L camera and the R camera, and FIG. 16 is a schematic diagram viewed from above the L camera and the R camera. In addition, FIG. 17 is an illustrative diagram showing amounts of camera shake detected by a sensor of the L camera and a sensor of the R camera.

Sensor planes SlT0 and SlT1 shown in FIG. 15 are sensor planes of the L camera at the times T0 and T1, and sensor planes SrT0 and SrT1 are sensor planes of the R camera at the times T0 and T1. In addition, points ClT0 and ClT1 shown in FIGS. 15 and 16 are centers of the L camera at the times T0 and T1, and points CrT0 and CrT1 are centers of the R camera at the times T0 and T1.

A point on a sensor plane of each of the cameras which corresponds to a point present in a real space is a point at which a line, which connects the center of the camera and the point present in the real space, intersects the sensor plane of the camera. For example, points MlT0 and MlT1 shown in FIGS. 15 to 17 are points on the sensor plane of the L camera corresponding to a point P present in the real space at the times T0 and T1. In addition, points MlT0 and MlT1 shown in FIGS. 15 to 17 are likewise points on the sensor plane of the R camera corresponding to the point P present in the real space at the times T0 and T1.

When the two cameras move (shake) during a time from the time T0 to the time T1 as shown in FIGS. 15 and 16, amounts of camera shake (amounts of movement of the same point on the sensor planes) of the cameras are different, as shown in FIG. 17. Thus, when camera shake correction for one camera is applied to the other camera without being changed, there is no guarantee that the amount of camera shake of the other camera is cancelled. In addition, it is known that, when camera shake of the cameras is corrected independently to cancel the different amounts of camera shake, it is difficult to perceive corrected images as being fused (which is a phenomenon in which a human recognizes left and right images as one image).

Thus, the present embodiment has been created focusing on the above-described circumstance. In the medical observation system 1 according to the present embodiment, a control device 20-3 performs camera shake correction for a reference camera selected on the basis of an input of a user with little deterioration in image quality, and performs camera shake correction for a camera other than the reference camera in accordance with the correction of the camera shake of the reference camera. An overview of camera shake correction according to the present embodiment will be described here with reference to FIG. 18.

Figure 18:
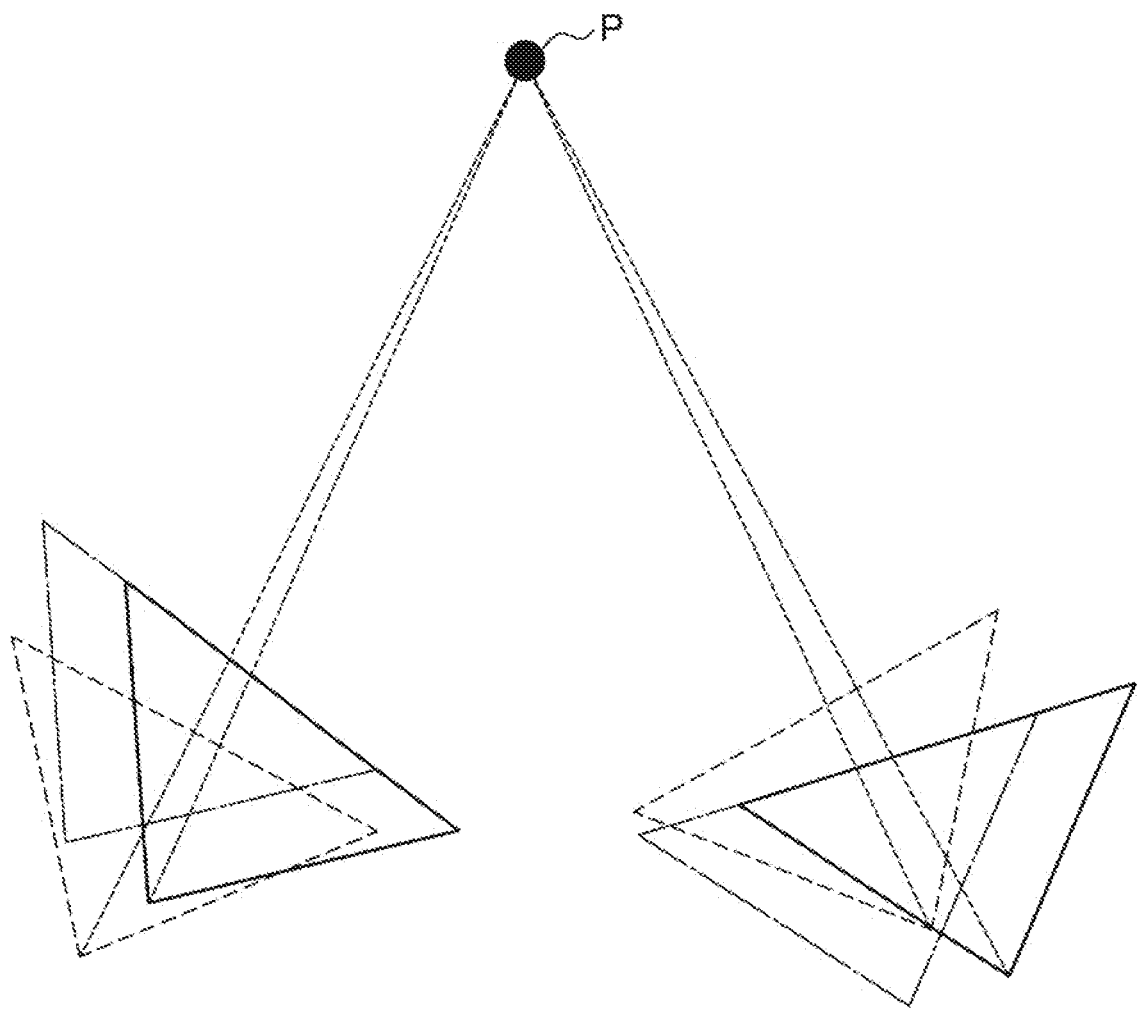
FIG. 18 is an illustrative diagram for describing the overview of camera shake correction according to the embodiment.

FIG. 18 is a schematic diagram viewed from above the L camera and the R camera. Camera shake correction is performed with little deterioration in image quality by only removing, for example, camera shake with respect to translational movements (movements in horizontal and vertical directions) rather than completely removing camera shake in the camera shake correction according to the present embodiment. In the camera shake correction according to the present embodiment, only the translational motions are cancelled among camera motions during the time from the time T0 to the time T1, and motions of rotational and expansion and contraction (movements in a front-back direction) components remain as shown in FIG. 18.

According to the present embodiment, deterioration in image quality is suppressed and a user can comfortably perceive stereoscopic images due to the camera shake correction of the reference camera as described above, and corrected images can be easily perceived to be fused due to the camera shake correction of the camera other than the reference camera as described above. A configuration of the control device 20-3 according to the present embodiment that brings such an effect will be described in detail below with reference to FIGS. 19 and 20.

3-2. Configuration of Third Embodiment (Control Device)

Figure 19:
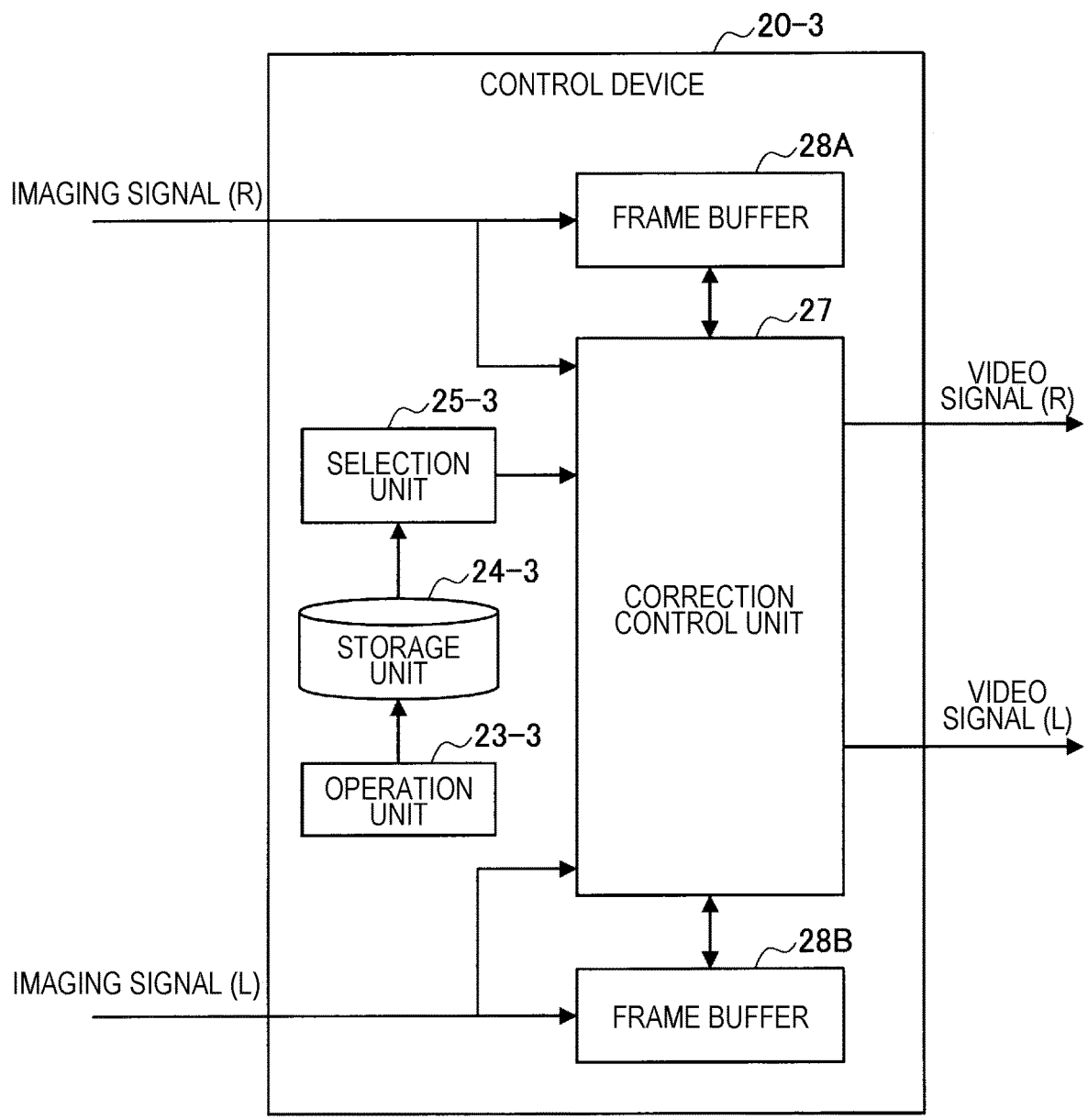
FIG. 19 is an illustrative diagram showing a configuration of a control device 20 according to the embodiment.

FIG. 19 is an illustrative diagram showing a configuration of the control device 20-3 included in the medical observation system 1 according to the present embodiment. The control device 20-3 is an information processing device that includes an operation unit 23-3, a storage unit 24-3, a selection unit 25-3, a correction control unit 27, and frame buffers 28A and 28B, as shown in FIG. 19.

The operation unit 23-3 receives an input of a user with respect to a selection of one reference camera which serves as a reference when correcting camera shake between two cameras (the L camera and the R camera) included in the endoscope device 10. The user may perform an input so that, for example, a camera corresponding to his or her dominant eye is set as a reference camera or a camera corresponding to an eye having high visual acuity between his or her left and right eyes is set as a reference camera. The user can select the reference camera which enables him or her to perceive stereoscopic images more comfortably by means of the operation unit 23-3.

The storage unit 24-3 stores selection information regarding the selection of the reference camera input by the user by means of the operation unit 23-3. The selection information stored by the storage unit 24-3 is provided to the selection unit 25-3, which will be described below. Since the selection information is stored by the storage unit 24-3 and provided to the selection unit 25-3, which will be described below, when, for example, the same user consecutively uses the medical observation system 1 a plurality of times, the user can save effort to perform selection operations in the second and following uses of the user.

The selection unit 25-3 reads the selection information regarding the selection of the reference camera from the storage unit 24-3 and selects one reference camera from the two cameras included in the endoscope device 10. In addition, the selection unit 25-3 provides information of the selected reference camera to the correction control unit 27.

The correction control unit 27 receives past corrected images from the frame buffers 28A and 28B and corrects camera shake of current images (imaging signals) supplied from the two cameras included in the endoscope device 10. In addition, the correction control unit 27 outputs the corrected videos by dividing the videos into a left-eye video signal (L) and a right-eye video signal (R) with which the display device 30 can display the videos. Furthermore, the correction control unit 27 provides a corrected right-eye image to the frame buffer 28A and a corrected left-eye image to the frame buffer 28B. Detailed configuration of the correction control unit 27 will be described below.

The frame buffers 28A and 28B receive and store the imaging signals (R) and (L) respectively supplied from the two cameras included in the endoscope device 10. In addition, the frame buffers 28A and 28B receive the corrected images from the correction control unit 27 and store the images. Furthermore, the frame buffers 28A and 28B provide the past corrected images to the correction control unit 27. The frame buffers 28A and 28B may have a mechanism which can automatically delete past images that have passed a predetermined period or past corrected images.

(Correction Control Unit)

The configuration of the control device 20-3 included in the medical observation system 1 according to the present embodiment has been described above. Next, a detailed configuration of the correction control unit 27 included in the control device 20-3 will be described with reference to FIG. 20.

Figure 20:
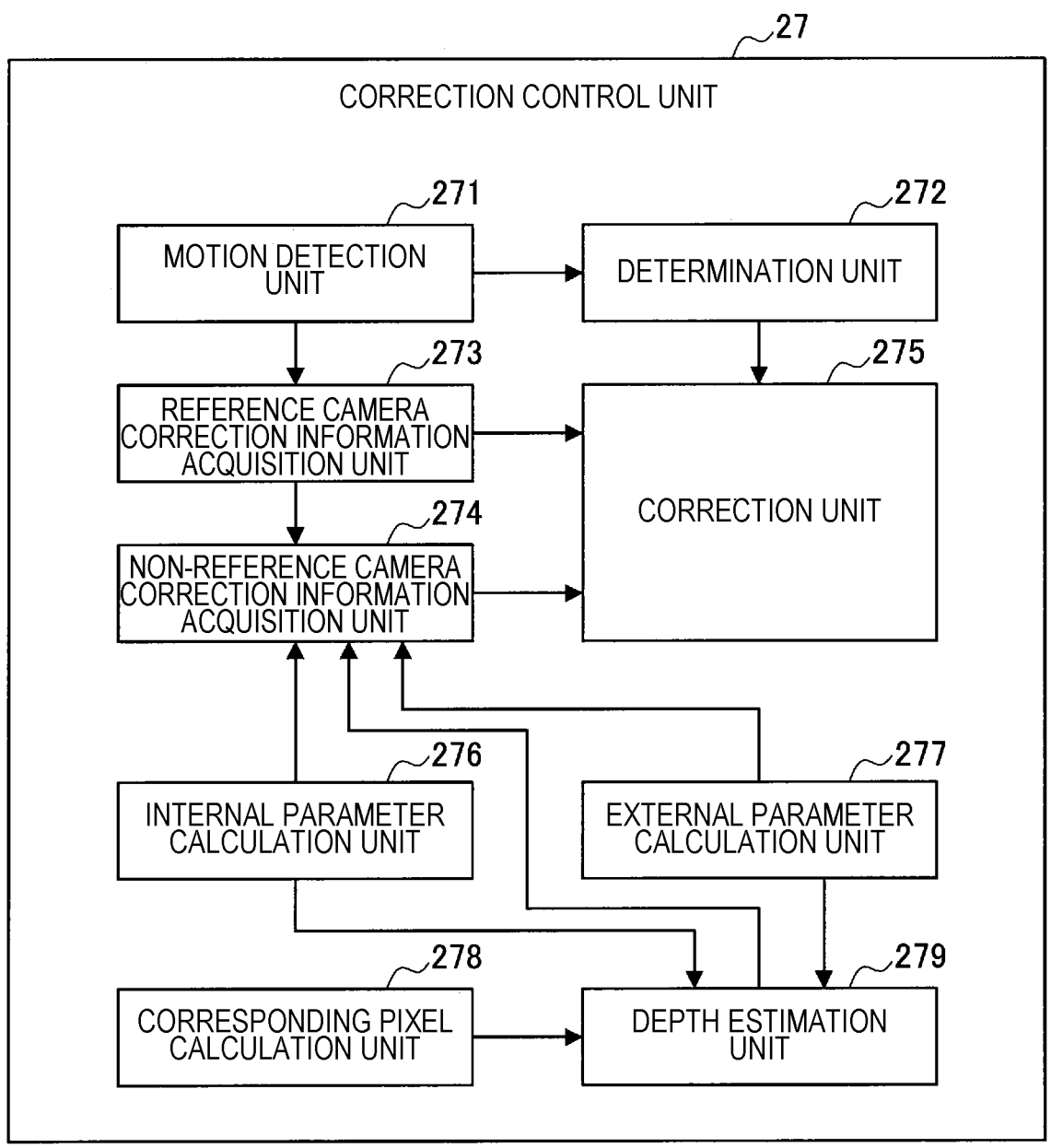
FIG. 20 is an illustrative diagram showing a configuration of a correction control unit 27 according to the embodiment.

FIG. 20 is an illustrative diagram showing the configuration of the correction control unit 27. The correction control unit 27 includes a motion detection unit 271, a determination unit 272, a reference camera correction information acquisition unit 273 (a first correction information acquisition unit), a non-reference camera correction information acquisition unit 274 (a second correction information acquisition unit), a correction unit 275, an internal parameter calculation unit 276, an external parameter calculation unit 277, a corresponding pixel calculation unit 278, and a depth estimation unit 279, as shown in FIG. 20.

The motion detection unit 271 detects a motion of the reference camera selected by the selection unit 25-3. For example, the motion detection unit 271 may detect the motion of the reference camera by comparing a current image acquired by the reference camera with an image obtained by performing camera shake correction on an image acquired by the reference camera in the past (a past corrected image). The motion detection unit 271 detects the motion of the reference camera by, for example, tracking characteristic points of the images such as a corner point detected in the current image and the past corrected image. As a method of tracking characteristic points of images and detecting motions of the images, for example, a Lucas-Kanade method or the like may be used. In addition, the motion of the reference camera detected by the motion detection unit 271 may include translational components, rotational components, and expansion and contraction components.

In addition, the motion detection unit 271 provides the detected motion of the reference camera to the determination unit 272 and the reference camera correction information acquisition unit 273.

The determination unit 272 determines whether or not the motion of the reference camera detected by the motion detection unit 271 is less than a threshold value, and provides a result of the determination to the correction unit 275. The determination unit 272 may determine, for example, whether each of a translational component (a movement in vertical and horizontal directions), a rotational component, and an expansion and contraction component (a movement in the front-back direction) included in the motion of the reference camera is less than a threshold value corresponding to the component.

The reference camera correction information acquisition unit 273 acquires reference camera correction information (first correction information) that lessens the motion of the reference camera detected by the motion detection unit 271 and provides the information to the correction unit 275.

For example, the reference camera correction information acquisition unit 273 may acquire the reference camera correction information to lessen the translational component (movement in the horizontal and vertical directions) and maintain the rotational component and the expansion and contraction component in the motion of the reference camera. The reference camera correction information acquired by the reference camera correction information acquisition unit 273 may be, for example, information including a vertical parameter for vertically moving an image acquired by the reference camera and a horizontal parameter for horizontally moving the image. If the correction is performed using the reference camera correction information described above, it is more difficult for deterioration in image quality that usually occurs in a corrected image of the reference camera to occur than in a case in which correction to attenuate (not to maintain) the rotational component and the expansion and contraction component is performed. Note that motions of a camera made when a body cavity of a patient is observed with an endoscope are mostly translational components, and thus an effect of reliably removing camera shake can be exhibited if correction is performed using such correction information.

In particular, the reference camera correction information acquisition unit 273 may acquire reference camera correction information including a vertical parameter and a horizontal parameter, in which the above-described vertical movement and horizontal movement are movements in units of the integer number of pixels. For example, the reference camera correction information acquisition unit 273 may calculate each of the parameters by calculating values of a vertical movement and a horizontal movement that offset the translational component included in the motion of the reference camera and then performing a rounding process such as rounding up, rounding down, and rounding the directional movements. If correction is performed using the above-described reference camera correction information, it is more difficult for deterioration in image quality that usually occurs in a corrected image of the reference camera to occur.

Note that the reference camera correction information acquired by the reference camera correction information acquisition unit 273 may have the form of a transformation matrix that can be used in a projective transformation of images.

The non-reference camera correction information acquisition unit 274 acquires non-reference camera correction information (second correction information) that lessens a motion of a camera other than the reference camera (a non-reference camera) included in the two cameras of the endoscope device 10 by using a method different from that of the reference camera correction information acquisition unit 273. In addition, the non-reference camera correction information acquisition unit 274 provides the acquired non-reference camera correction information to the correction unit 275.

The non-reference camera correction information acquisition unit 274 may acquire the non-reference camera correction information on the basis of, for example, corresponding pixel information regarding corresponding pixels that are included in an image acquired by the reference camera and an image acquired by the non-reference camera. The non-reference camera correction information may include, for example, a vertical parameter for vertically moving each pixel of the image acquired by the non-reference camera. Furthermore, the non-reference camera correction information acquisition unit 274 may acquire the non-reference camera correction information so that the vertical parameter included in the non-reference camera correction information and the vertical parameter included in the reference camera correction information are the same as each other for the corresponding pixels. According to this configuration, movements of the corresponding pixels in the vertical direction after correction are the same in the images acquired by the reference camera and the non-reference camera, and thus corrected images can easily perceived to be fused. Note that the above-described corresponding pixel information may be provided from the depth estimation unit 279, which will be described below, to the non-reference camera correction information acquisition unit 274.

In addition, the non-reference camera correction information acquisition unit 274 may acquire the non-reference camera correction information on the basis of calibration information of the two cameras of the endoscope device 10 and further of depth information of a subject captured by the two cameras, in addition to the corresponding pixel information. The calibration information may include an internal parameter including information such as focal lengths of the cameras and an external parameter including information of a relation between relative positions and attitudes of the cameras. An example of a method for acquiring the non-reference camera correction information based on the above-described information will be described below with reference to FIGS. 22 to 25. Note that the non-reference camera correction information acquisition unit 274 may be provided with the internal parameter from the internal parameter calculation unit 276 and the external parameter from the external parameter calculation unit 277, and both of the units will be described below.

When the determination unit 272 determines that the motion of the reference camera is less than the threshold value, the correction unit 275 performs correction on the image acquired by the reference camera on the basis of the reference camera correction information. If the correction is performed on the basis of the reference camera correction information when the translational component included in the motion of the reference camera is large, there is concern that an image is significantly moved due to the correction, and thus, for example, is not displayed on the display device 30 (a part of or the entire image moves outside a screen). Furthermore, if the rotational component and the expansion and contraction component included in the motion of the reference camera are large, it is not possible to sufficiently remove the influence of camera shake in the correction based on the reference camera correction information in which the rotational component and the expansion and contraction component are maintained. Thus, the correction unit 275 may not perform correction on the images when the determination unit 272 determines that the motion of the reference camera is greater than or equal to the threshold value. According to this configuration, when the motion of the reference camera is great, normal images are displayed without deteriorated image quality while the influence of camera shake remains.

In addition, when the determination unit 272 determines that the motion of the reference camera is less than the threshold value, the correction unit 275 performs correction on the image acquired by the non-reference camera on the basis of the non-reference camera correction information. Thus, the correction performed by the correction unit 275 on the image acquired by the non-reference camera may cause significant deterioration in image quality when compared to the correction on the image acquired by the reference camera. According to this configuration, a corrected image of the reference camera selected on the basis of an input of the user is displayed with less deterioration in image quality when compared to a corrected image of the non-reference camera.

The internal parameter calculation unit 276 calculates an internal parameter of the cameras of the endoscope device 10. For example, the internal parameter calculation unit 276 may calculate the internal parameter using images obtained when the cameras capture a known calibration graphic pattern. The internal parameter calculated by the internal parameter calculation unit 276 is provided to the non-reference camera correction information acquisition unit 274 and the depth estimation unit 279.

The external parameter calculation unit 277 calculates an external parameter including information of a relation between relative positions and attitudes of the two cameras of the endoscope device 10. For example, the external parameter calculation unit 277 may calculate the external parameter using images obtained when the two cameras capture the known calibration graphic pattern. The external parameter calculated by the external parameter calculation unit 277 is provided to the non-reference camera correction information acquisition unit 274 and the depth estimation unit 279.

The corresponding pixel calculation unit 278 calculates a correspondence between pixels of the image acquired by the reference camera and the image acquired by the non-reference camera, thereby acquiring the corresponding pixel information. The corresponding pixel calculation unit 278 may calculate the correspondence between the pixels of the images using, for example, block matching. The acquired corresponding pixel information is provided to the depth estimation unit 279.

The depth estimation unit 279 acquires depth information on the basis of the corresponding pixel information, the internal parameter, and the external parameter. In addition, the depth estimation unit 279 provides the corresponding pixel information and the depth information to the non-reference camera correction information acquisition unit 274.

3-3. Operation of Third Embodiment

Figure 21:
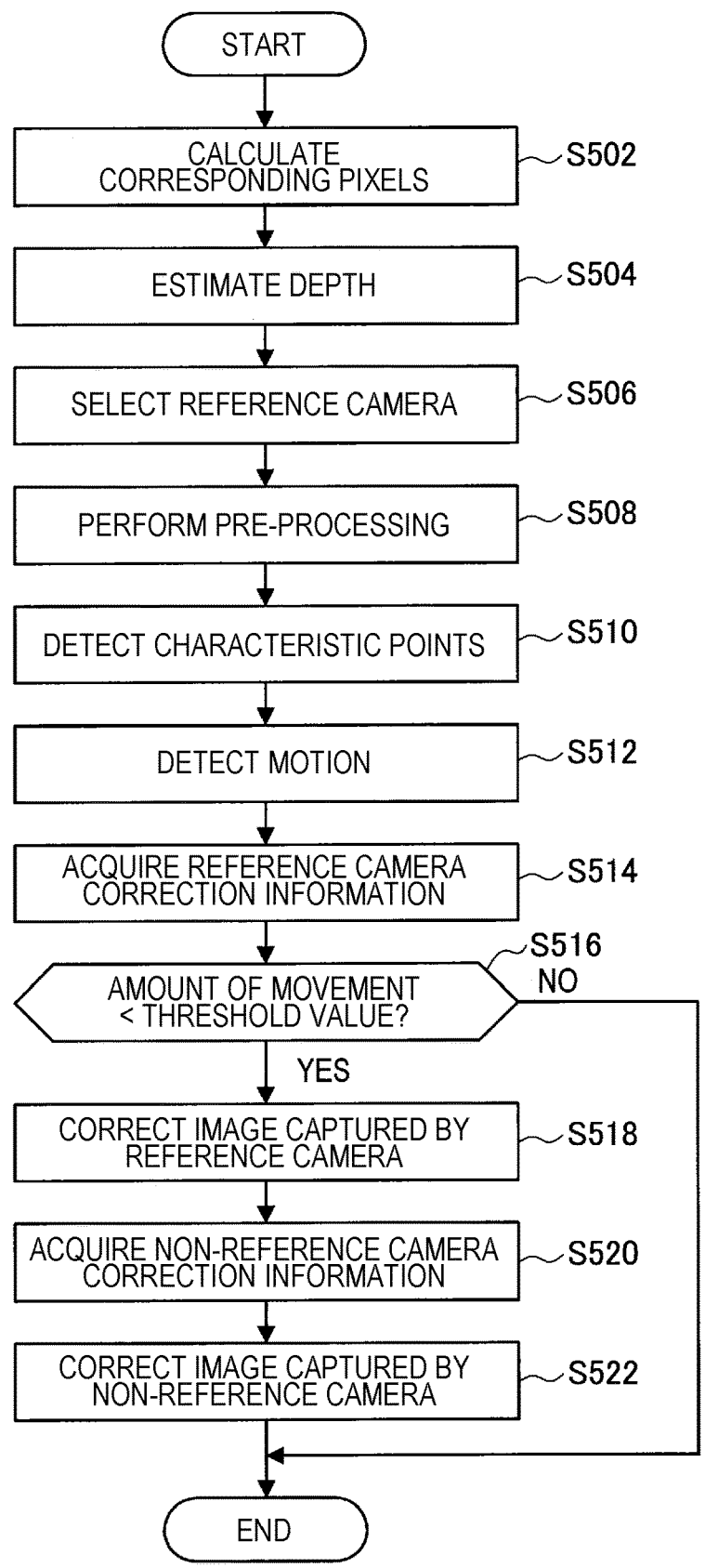
FIG. 21 is a flowchart for describing an operation of a medical observation system 1 according to the embodiment.

The example of the configuration of the control device 20-3 included in the medical observation system 1 according to the third embodiment of the present disclosure has been described above. Next, an example of an operation of the medical observation system 1 according to the present embodiment will be described with reference to FIGS. 21 to 25. FIG. 21 is a flowchart showing an example of a camera shake correction operation performed in the medical observation system 1 according to the present embodiment. Although the medical observation system 1 according to the present embodiment performs a selection information setting process and a camera shake correction process shown in FIG. 21, the selection information setting process is similar to the selection information setting process performed in the medical observation system 1 according to the first embodiment described with reference to FIG. 4, and thus description thereof will be omitted. FIGS. 22 to 25 are illustrative diagrams for describing an example of a method for acquiring non-reference camera correction information by the non-reference camera correction information acquisition unit 274 during camera shake correction in the medical observation system 1 according to the present embodiment. The example of the camera shake correction operation performed in the medical observation system 1 according to the present embodiment will be described with reference to FIG. 21, and then the example of the method for acquiring non-reference camera correction information by the non-reference camera correction information acquisition unit 274 will be described with reference to FIGS. 22 to 25 below.

(Camera Shake Correction Process)

First, the corresponding pixel calculation unit 278 calculates a correspondence between pixels of an image acquired by a reference camera and an image acquired by a non-reference camera, and thereby acquires corresponding pixel information (S502), as shown in FIG. 21. Then, the depth estimation unit 279 acquires depth information on the basis of the corresponding pixel information, an internal parameter, and an external parameter (S504).

Then, the selection unit 25-3 reads selection information regarding a selection of the reference camera from the storage unit 24-3 and provides the information to the correction control unit 27 (S506). The motion detection unit 271 of the correction control unit 27 that has received the selection information performs pre-processing such as noise removal on the image acquired by the reference camera and a past corrected image of the reference camera read from the frame buffer 28A or 28A (S508). Next, the motion detection unit 271 detects characteristic points such as a corner point in the images (S510). Furthermore, the motion detection unit 271 tracks the characteristics points of the images using the Lucas-Kanade method and thereby detects a motion of the reference camera (S512). Here, the motion detection unit 271 may calculate the motion of the reference camera for each component.

Next, the reference camera correction information acquisition unit 273 acquires reference camera correction information on the basis of the motion of the reference camera (S514). Further, the determination unit 272 determines whether or not the motion (an amount of movement) of the reference camera is less than a threshold value (S516). When the determination unit 272 has determined that the motion of the reference camera is greater than or equal to the threshold value (No in S516), the camera shake correction process ends without performing correction on the image.

On the other hand, when the determination unit 272 has determined that the motion of the reference camera is less than the threshold value (Yes in S516), the correction unit 275 performs correction on the image acquired through capturing of the reference camera with little deterioration in image quality on the basis of the reference camera correction information (S518).

Next, the non-reference camera correction information acquisition unit 274 acquires non-reference camera correction information (S520). A non-reference camera correction information acquisition process of Step S520 will be described below with reference to FIGS. 22 to 25.

Finally, the correction unit 275 performs correction on the image acquired through capturing of the non-reference camera on the basis of the non-reference camera correction information (S522).

(Non-Reference Camera Correction Information Acquisition Process)

The example of the camera shake correction operation performed in the medical observation system 1 according to the present embodiment has been described above. Next, a method for acquiring the non-reference camera correction information in the non-reference camera correction information acquisition process of Step S520 included in the above-described camera shake correction process will be described with reference to FIGS. 22 to 25. FIGS. 22 to 25 are illustrative diagrams for describing an example of the method for acquiring the non-reference camera correction information according to the present embodiment.

Figure 22:
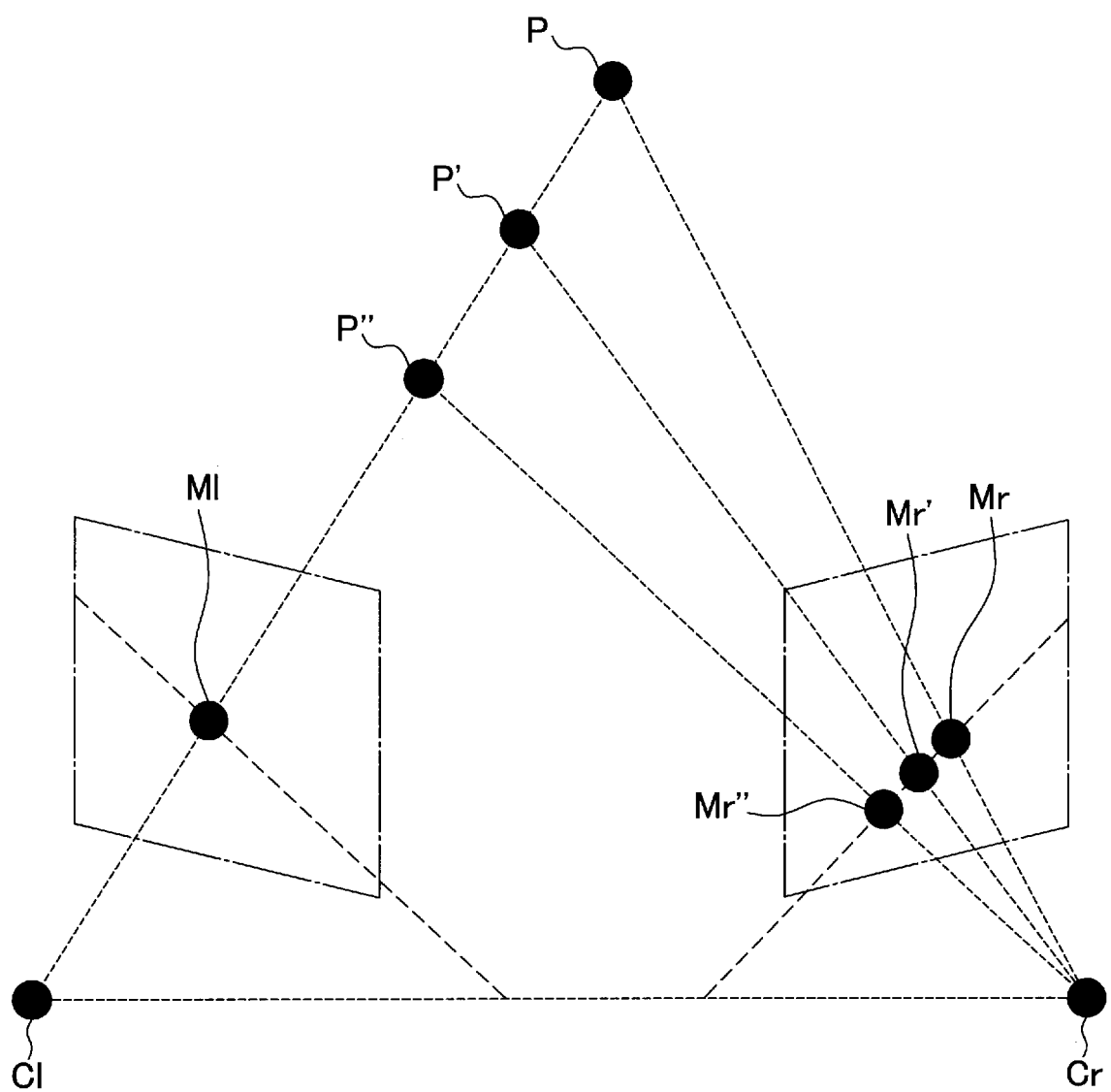
FIG. 22 is an illustrative diagram for describing a method for acquiring non-reference camera correction information according to the embodiment.

FIG. 22 is a schematic diagram obtained by viewing an L camera and an R camera that are capturing a point P present in a real space from a rear side. Cl and Cr shown in FIG. 22 are the center of the L camera and the center of the R camera, respectively.

A point Ml and a point Mr shown in FIG. 22 are points on sensor planes of the L camera and the R camera corresponding to the same point P present in the real space, and the point Ml and the point Mr can be referred to as corresponding pixels.

Here, a relation of homogenous coordinates $m_l$ and $m_r$ of the points Ml and Mr on two camera sensor planes is expressed with the following formula using a basic matrix F obtained using an internal parameter and an external parameter.

[Math. 1]

$$m_l^T F m_r = 0 \quad (1)$$

Figure 23:
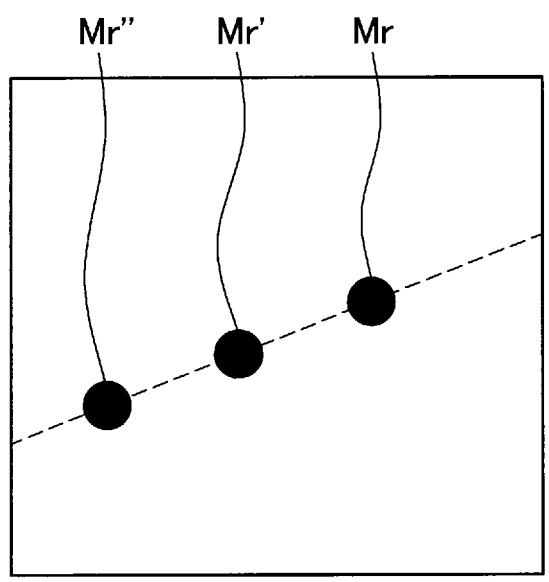
FIG. 23 is an illustrative diagram for describing a method for acquiring non-reference camera correction information according to the embodiment.

Here, when $m_l$ is given, it is not possible to specify the constant $m_r$ using the above formula. FIG. 23 is an illustrative diagram showing examples of candidates for the point Mr on the sensor plane of the R camera specified using the above formula when the homogenous coordinate mi of the point Ml is given. As shown in FIG. 23, the point Mr can be specified only as being present on a straight line. That is, numerous points including points Mr, Mr', Mr'', and the like corresponding to points P, P', P'', and the like, which are shown in FIG. 22 and present on the straight line, are candidates.

Figure 24:
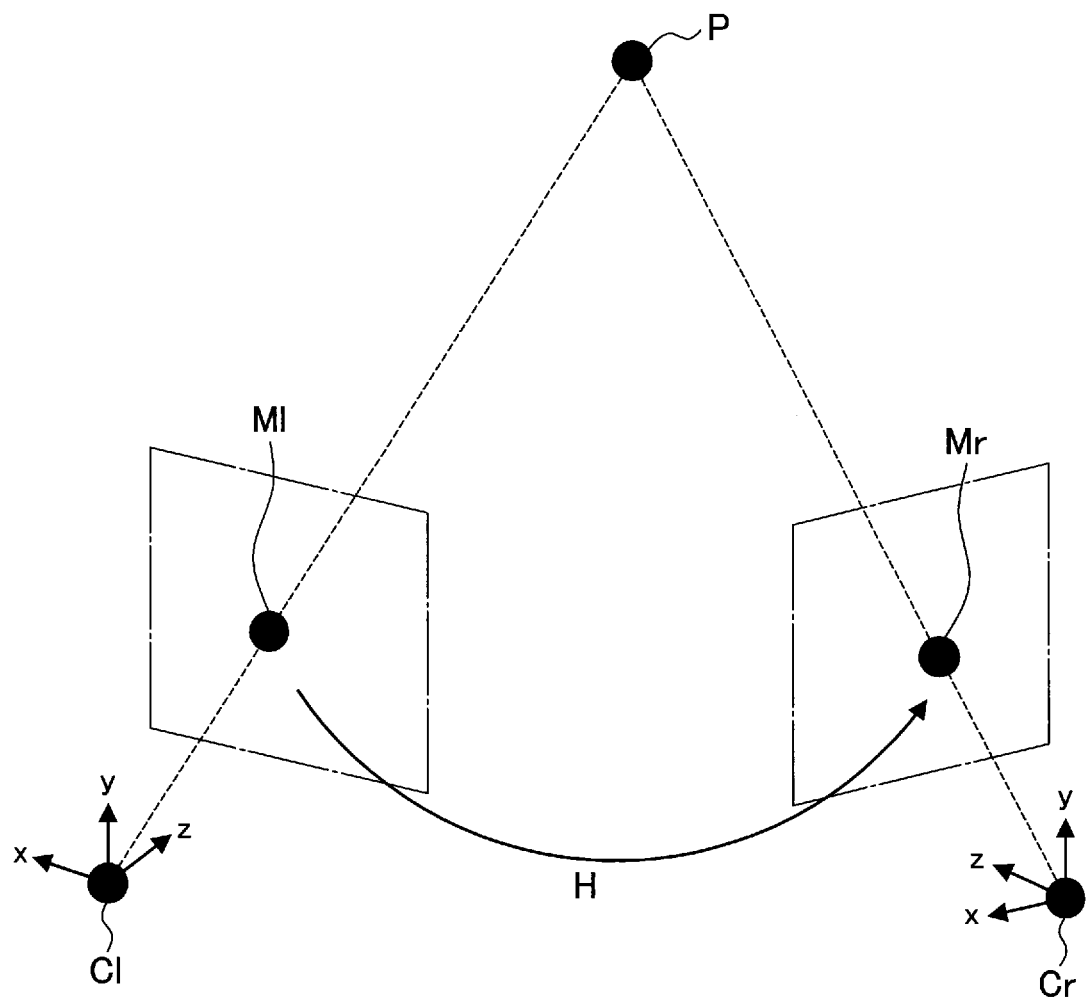
FIG. 24 is an illustrative diagram for describing a method for acquiring non-reference camera correction information according to the embodiment.

Thus, $m_r$ is specified further using depth information. FIG. 24 is a schematic diagram obtained by viewing the L camera and the R camera capturing the point P present in the real space from a rear side. Since points Ml, Mr, Cl, and Cr shown in FIG. 24 are similar to the points Ml, Mr, Cl, and Cr described with reference to FIG. 22, description thereof will be omitted.

Here, it is assumed that the coordinate of the point P present in the real space viewed in a three-dimensional coordinate system having the center Cl of the L camera as the origin is $p_l$ and the coordinate of the point P present in the real space viewed from a three-dimensional coordinate system having the center Cr of the R camera as the origin is $p_r$. A relation between $p_l$ and $p_r$ is expressed with the following formula using an external parameter matrix [R|t] between the L camera and the R camera. Note that R represents a matrix indicating a rotational component, and t represents a matrix indicating translational and expansion and contraction components.

[Math. 2]

$$p_l [R|t] p_r \quad (2)$$

In addition, pi and the homogeneous coordinate mi on a sensor plane corresponding to the point P generally have a relation of the following formula using an internal parameter matrix $A_l$ of the L camera. Note that hi is a coefficient that changes in accordance with a depth value of the point P with respect to the L camera.

[Math. 3]

$$h_l m_l = A_l p_l \quad (3)$$

In addition, $p_r$ and $m_r$ similarly satisfy the following formula. Note that $h_r$ is a coefficient that changes in accordance with a depth value of the R camera with respect to the point P.

[Math. 4]

$$h_r m_r A_r p_r \quad (4)$$

A relation of following formula is obtained if the formulas (2) to (4) are solved with respect to $m_r$.

$$m_r = hHm_l \quad \text{[Math. 5]}$$

However, $h = \dfrac{h_l}{h_r}$, $H = A_r [R|t] A_l^{-1}$

Here, the coefficient h can be specified from a depth value of each camera with respect to the point P obtained using the depth information. In addition, the matrix H is specified from the internal parameter and the external parameter as described above. Thus, when $m_l$ is given, $m_r$ can be obtained on the basis of the internal parameter, the external parameter, and the depth information as described above. The above-described operation can be applied to the acquisition of the non-reference camera correction information in the non-reference camera correction information acquisition process.

Figure 25:
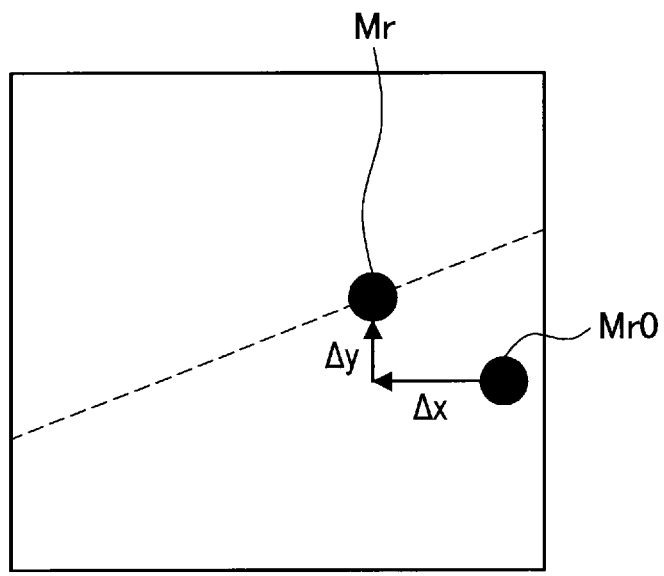
FIG. 25 is an illustrative diagram for describing a method for acquiring non-reference camera correction information according to the embodiment.

For example, if mi is set as a homogeneous coordinate of each pixel in a corrected image of the reference camera when the L camera is the reference camera, a homogeneous coordinate of a pixel corresponding to mi in a corrected image of the non-reference camera is calculated as $m_r$. FIG. 25 is an illustrative diagram showing an amount of correction of the non-reference camera corresponding to the point Mr. A point Mr0 shown in FIG. 25 is a point corresponding to the point P on a sensor plane of the non-reference camera before correction. Thus, the amount of correction of the non-reference camera corresponding to the point Mr is acquired as Δx in the horizontal direction and Δy in the vertical direction, as shown in FIG. 25. The non-reference camera correction information can be acquired if amounts of correction are acquired for all pixels of the non-reference camera in that manner. Note that the non-reference camera correction information can be acquired in the same way when the R camera is the reference camera.

3-4. Effect of Third Embodiment

The control device 20-3 according to the third embodiment has been described above in detail. According to the present embodiment, the control device 20-3 performs camera shake correction entailing little deterioration in image quality for a reference camera selected on the basis of an input of a user, and performs camera shake correction for a non-reference camera in accordance with the camera shake correction of the reference camera. A user can comfortably perceive stereoscopic images due to the camera shake correction for the reference camera entailing little deterioration in image quality. In addition, a corrected image can be easily perceived to be fused due to the camera shake correction for the non-reference camera in accordance with the camera shake correction of the reference camera.

3-5. Modified Examples of Third Embodiment

The third embodiment of the present disclosure has been described above. Several modified examples of the present embodiment will be described below. Note that each of the modified examples to be described below may be applied to the present embodiment alone or as a combination. In addition, each of the modified examples may be applied in place of or in addition to the configuration described in the present embodiment.

Modified Example 1

The number of pieces of selection information stored in the storage unit 24-3 according to the present embodiment is not limited to one as in the modified example 1 of the first embodiment. The storage unit 24-3 according to the present embodiment may store, for example, selection information in association with user information regarding a user for each user. According to this configuration, when the medical observation system 1 has a function of authenticating users, for example, a user for whom selection information is stored in association with his or her user ID and for whom authentication has been performed can save effort of selecting a reference camera.

Modified Example 2

Although the case in which the correction unit 275 does not perform correction when the determination unit 272 determines that the motion of the reference camera is greater than or equal to the threshold value has been described above, the present technology is not limited thereto. For example, when the determination unit 272 determines that a rotational component and an expansion and contraction component included in a motion of the reference camera are greater than or equal to the threshold value, the correction unit 275 may perform correction to cancel the rotational component and the expansion and contraction component in addition to a translational component. According to this configuration, correction of camera shake can be performed with little deterioration in image quality caused by the correction even when a motion of the reference camera is significant.

Modified Example 3

Like the selection of the reference lens described in the modified example 4 according to the first embodiment, a selection of a reference camera according to the present embodiment is not limited to being made on the basis of an input of a user. For example, the selection unit 25-3 according to the present embodiment may select the reference lens on the basis of images acquired by the two cameras of the endoscope device 10.

For example, like the selection of a reference lens described in the modified example 4 according to the first embodiment, the selection unit 25-3 may recognize a subject on the basis of the two images acquired by the two cameras and select the reference camera in accordance with a position or a size of the subject. Since the selection of the reference camera in accordance with the position and the size of the subject is similar to the selection of the reference lens described in the modified example 4 according to the first embodiment, a description thereof will be omitted.

Since the reference camera is automatically selected in accordance with the subject according to this configuration, a user can save effort of selecting a reference camera.

4. Example of Hardware Configuration

The embodiments and modified examples of the present disclosure have been described above. The above-described selection information setting process, driving control process, and information processing such as the camera shake correction process are realized through cooperation of software and hardware of the control device 20 (the control devices 20-1, 20-2, or 20-3), which will be described below.

Figure 26:
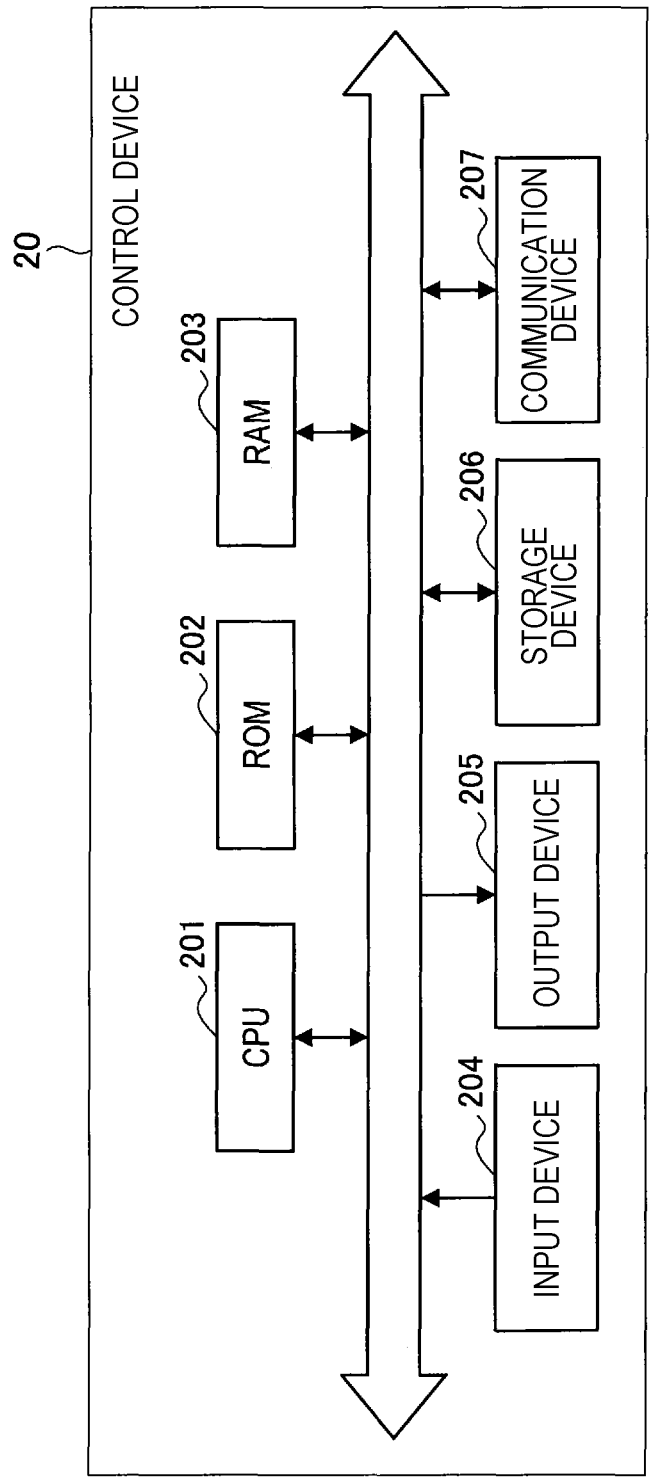
FIG. 26 is an illustrative diagram showing an example of a hardware configuration of a control device 20 according to the embodiment.

FIG. 26 is an illustrative diagram showing a hardware configuration of the control device 20. The control device 20 includes a central processing unit (CPU) 201, a read only memory (ROM) 202, a random access memory (RAM) 203, an input device 204, an output device 205, a storage device 206, and a communication device 207 as illustrated in FIG. 26.

The CPU 201 functions as an arithmetic processing device and a control device to control overall operations of the control device 20 in accordance with various programs. In addition, the CPU 201 may be a micro-processor. The ROM 202 stores programs, arithmetic operation parameters, and the like to be used by the CPU 201. The RAM 203 temporarily stores programs to be used to execute the CPU 201, parameters that are changed appropriately for the execution, and the like. These components are connected to each other by a host bus configured as a CPU bus. Functions of the video processing units 21A and 21B, the movement control unit 26-1, 26-2A, and 26-2B, the correction control unit 27, and the like are mainly realized through, for example, cooperation of the CPU 201, the ROM 202, the RAM 203, and software.

The input device 204 is constituted by an input means such as a mouse, a keyboard, a touch panel, a button, a microphone, a switch, and a lever for inputting information by a user and an input control circuit that generates an input signal on the basis of the input of the user and outputs the signal to the CPU 201. The user of the control device 20 can input various kinds of data to the control device 20 or instruct the control device to perform processing operations by operating the input device 204. The input device 204 corresponds to the operation units 23 and 23-3.

The output device 205 includes a display device, for example, a liquid crystal display (LCD) device, an OLED device, a lamp, or the like. Further, the output device 205 includes an audio output device such as a speaker and a headphone. The display device displays, for example, a captured image, a generated image, and the like. Meanwhile, the audio output device converts audio data and the like into a sound and outputs the sound.

The storage device 206 is a device for data storage. The storage device 206 may include a storage medium, a recording device that records data in the storage medium, a reading device that reads the data from the storage medium, a deleting device that deletes the data recorded in the storage medium, and the like. The storage device 206 stores programs to be executed by the CPU 201 and various kinds of data. The storage device 206 corresponds to the storage unit 24.

The communication device 207 is a communication interface configured as, for example, a communication device for connecting to a communication network. In addition, the communication device 207 may include a wireless local area network (LAN)-applicable communication device, a Long Term Evolution (LTE)-applicable communication device, a wired communication device that performs wired communication, or a Bluetooth communication device.

5. Conclusion

According to an embodiment of the present disclosure, proper focus adjustment is possible as described above.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although the case in which a medical observation system includes an endoscope device and the endoscope device, which includes cameras (imaging units) including image sensors, performs photographing has been described in the embodiments, the present technology is not limited thereto. For example, another device with two or more cameras may perform photographing instead of the endoscope device. For example, the present technology may be applied to a medical observation system in which a video endoscope with two or more cameras (imaging units) that capture microscopic images is provided instead of the endoscope device.

In addition, although the each of the examples of the medical observation system having an endoscope device, a control device, and a display device has been described in the embodiments, the present technology is not limited thereto. For example, an embodiment of the present disclosure may be a medical observation device having the above-described functions of the endoscope device, the control device, and the display device. In addition, an embodiment of the present disclosure may be a video microscope device having the above-described functions of the video microscope, the control device, and the display device.

Further, according to the present embodiment, a computer program for causing hardware, such as the CPU 201, ROM 202, or RAM 203, to function similarly to that of each constituent element of the control device 20 can also be provided. In addition, a recording medium in which the computer program is recorded can also be provided.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
A medical observation device including:
an evaluation value calculation unit configured to calculate a focus evaluation value indicating a focus state of a lens for each of two or more lenses; and
a movement control unit configured to specify a lens movement parameter that is common to the two or more lenses on the basis of the focus evaluation value.

(2)
The medical observation device according to (1), further including:
a selection unit configured to select one reference lens from the two or more lenses.

(3)
The medical observation device according to (2), in which the movement control unit specifies a lens movement parameter that is common to the two or more lenses on the basis of a focus evaluation value corresponding to the selected reference lens.

(4)
The medical observation device according to (3), in which the movement control unit specifies the lens movement parameter that is common to the two or more lenses without using the focus evaluation value corresponding to a lens other than the reference lens among the focus evaluation values.

(5)
The medical observation device according to any one of (2) to (4), in which the movement control unit specifies, as the lens movement parameter that is common to the two or more lenses, a parameter acquired from a weighted average of a lens movement parameter specified on the basis of the focus evaluation value corresponding to the reference lens and a lens movement parameter specified on the basis of the focus evaluation value corresponding to a lens other than the reference lens.

(6)
The medical observation device according to (5), in which the movement control unit acquires the weighted average by setting a weight of the lens movement parameter specified on the basis of the focus evaluation value corresponding to the reference lens to be greater than a weight of the lens movement parameter specified on the basis of the focus evaluation value corresponding to the lens other than the reference lens.

(7)
The medical observation device according to any one of (2) to (6), further including: an operation unit configured to receive an input with respect to a selection of the reference lens.

(8)
The medical observation device according to any one of (2) to (7), further including: a storage unit configured to store selection information regarding a selection of the reference lens.

(9)
The medical observation device according to (8), in which the storage unit stores the selection information in association with user information regarding a user for each user.

(10)
The medical observation device according to (1), in which the movement control unit specifies, as the lens movement parameter that is common to the two or more lenses, an average value of lens movement parameters of the two or more lenses specified on the basis of the focus evaluation values calculated for the two or more lenses.

(11)
The medical observation device according to any one of (1) to (10), further including:
an imaging unit including an image sensor.

(12)
A lens driving control device including:
an evaluation value calculation unit configured to calculate a focus evaluation value indicating a focus state of each of two or more lenses for each of the lenses; and
a movement control unit configured to specify a lens movement parameter that is common to the two or more lenses on the basis of the focus evaluation value.

(13)
A lens driving control method including:
calculating a focus evaluation value indicating a focus state of a lens for each of two or more lenses; and
specifying, by a processor, a lens movement parameter that is common to the two or more lenses on the basis of the focus evaluation value.

(14)
A program causing a computer to perform:
a process of calculating a focus evaluation value indicating a focus state of a lens for each of two or more lenses; and
a process of specifying, by a processor, a lens movement parameter that is common to the two or more lenses on the basis of the focus evaluation value.

(15)
A video microscope device including:
an evaluation value calculation unit configured to calculate a focus evaluation value indicating a focus state of a lens for each of two or more lenses;
a movement control unit configured to specify a lens movement parameter that is common to the two or more lenses on the basis of the focus evaluation value; and
an imaging unit including an image sensor,
in which the imaging unit captures a microscopic image.

(16)

A medical observation device including:
an evaluation value calculation unit configured to calculate a focus evaluation value indicating a focus state of a lens for each of two or more lenses;
a selection unit configured to select one reference lens from the two or more lenses; and
a movement control unit configured to specify a lens movement parameter for each of the two or more lenses on the basis of the focus evaluation value,
in which the evaluation value calculation unit sets a method for calculating the focus evaluation value corresponding to a lens other than the reference lens on the basis of the focus evaluation value corresponding to the reference lens.

REFERENCE SIGNS LIST 1 medical observation system
10 endoscope device
12 camera
14 lens driving unit
20 control device
21 video processing unit
22 evaluation value calculation unit
23 operation unit
24 storage unit
25 selection unit
26 movement control unit
27 correction control unit
28 frame buffer
30 display device
122 focus adjusting lens
124 image sensor
271 detection unit
272 determination unit
273 reference camera correction information acquisition unit
274 non-reference camera correction information acquisition unit
275 correction unit
276 internal parameter calculation unit
277 external parameter calculation unit
278 corresponding pixel calculation unit
279 depth estimation unit

The invention claimed is:

1. A medical observation device, comprising:
an evaluation value calculation unit configured to calculate a plurality of focus evaluation values, wherein each of the plurality of focus evaluation values indicates a focus state of a corresponding lens of a plurality of lenses;
a selection unit configured to select a reference lens from the plurality of lenses; and
a movement control unit configured to:
determine a first lens movement parameter based on a first focus evaluation value of the plurality of focus evaluation values, wherein the first focus evaluation value corresponds to the selected reference lens;
determine a second lens movement parameter based on a second focus evaluation value of the plurality of focus evaluation values, wherein
the second focus evaluation value corresponds to a lens of the plurality of lenses, and
the lens is different from the selected reference lens;
calculate a weighted average of the first lens movement parameter and the second lens movement parameter; and
determine a common lens movement parameter based on the weighted average of the first lens movement parameter and the second lens movement parameter, wherein the common lens movement parameter is common to each of the plurality of lenses.

2. The medical observation device according to claim 1, wherein the movement control unit is further configured to calculate the weighted average based on the first lens movement parameter that is greater than the second lens movement parameter.

3. The medical observation device according to claim 1, further comprising an operation unit configured to receive an input, wherein the input corresponds to the selection of the reference lens from the plurality of lenses.

4. The medical observation device according to claim 1, further comprising a storage unit configured to store selection information, wherein the selection information is associated with the selection of the reference lens from the plurality of lenses.

5. The medical observation device according to claim 4, wherein
the storage unit is further configured to store the selection information in association with user information, and
the user information is associated with a user of a plurality of users.

6. The medical observation device according to claim 1, wherein the movement control unit is further configured to:
determine a plurality of lens movement parameters corresponding to the plurality of lenses based on the plurality of focus evaluation values of the plurality of lenses;
determine an average value of the plurality of lens movement parameters; and
determine the common lens movement parameter based on the average value of the plurality of lens movement parameters.

7. The medical observation device according to claim 1, further comprising an imaging unit, wherein the imaging unit comprises an image sensor.

8. A lens driving control device, comprising:
an evaluation value calculation unit configured to calculate a plurality of focus evaluation values, wherein each of the plurality of focus evaluation values indicates a focus state of a corresponding lens of a plurality of lenses;
a selection unit configured to select a reference lens from the plurality of lenses; and
a movement control unit configured to:
determine a first lens movement parameter based on a first focus evaluation value of the plurality of focus evaluation values, wherein the first focus evaluation value corresponds to the selected reference lens;
determine a second lens movement parameter based on a second focus evaluation value of the plurality of focus evaluation values, wherein
the second focus evaluation value corresponds to a lens of the plurality of lenses, and
the lens is different from the selected reference lens;
calculate a weighted average of the first lens movement parameter and the second lens movement parameter; and
determine a common lens movement parameter based on the weighted average of the first lens movement parameter and the second lens movement parameter, wherein the common lens movement parameter is common to each of the plurality of lenses.

9. A lens driving control method, comprising:
calculating a plurality of focus evaluation values, wherein each of the plurality of focus evaluation values indicates a focus state of a corresponding lens of a plurality of lenses;
selecting a reference lens from the plurality of lenses;
determining a first lens movement parameter based on a first focus evaluation value of the plurality of focus evaluation values, wherein the first focus evaluation value corresponds to the selected reference lens;
determining a second lens movement parameter based on a second focus evaluation value of the plurality of focus evaluation values, wherein
the second focus evaluation value corresponds to a lens of the plurality of lenses, and
the lens is different from the selected reference lens;
calculating a weighted average of the first lens movement parameter and the second lens movement parameter; and
determining a common lens movement parameter based on the weighted average of the first lens movement parameter and the second lens movement parameter, wherein the common lens movement parameter is common to each of the plurality of lenses.

10. A non-transitory computer-readable medium having stored thereon computer-executable instructions which, when executed by a computer, cause the computer to execute operations, the operations comprising:
calculating a plurality of focus evaluation values, wherein each of the plurality of focus evaluation values indicates a focus state of a corresponding lens of a plurality of lenses;
selecting a reference lens from the plurality of lenses;
determining a first lens movement parameter based on a first focus evaluation value of the plurality of focus evaluation values, wherein the first focus evaluation value corresponds to the selected reference lens;
determining a second lens movement parameter based on a second focus evaluation value of the plurality of focus evaluation values, wherein
the second focus evaluation value corresponds to a lens of the plurality of lenses, and
the lens is different from the selected reference lens;
calculating a weighted average of the first lens movement parameter and the second lens movement parameter; and
determining a common lens movement parameter based on the weighted average of the first lens movement parameter and the second lens movement parameter, wherein the common lens movement parameter is common to each of the plurality of lenses.

11. A video microscope device, comprising:
an evaluation value calculation unit configured to calculate a plurality of focus evaluation values, wherein each of the plurality of focus evaluation values indicates a focus state of a corresponding lens of a plurality of lenses;
a selection unit configured to select a reference lens from the plurality of lenses;
a movement control unit configured to:
determine a first lens movement parameter based on a first focus evaluation value of the plurality of focus evaluation values, wherein the first focus evaluation value corresponds to the selected reference lens;
determine a second lens movement parameter based on a second focus evaluation value of the plurality of focus evaluation values, wherein
the second focus evaluation value corresponds to a lens of the plurality of lenses, and
the lens is different from the selected reference lens;
calculate a weighted average of the first lens movement parameter and the second lens movement parameter; and
determine a common lens movement parameter based on the weighted average of the first lens movement parameter and the second lens movement parameter, wherein the common lens movement parameter is common to each of the plurality of lenses; and
an imaging unit that comprises an image sensor, wherein the image sensor is configured to capture a microscopic image.

12. A medical observation device, comprising:
an evaluation value calculation unit configured to calculate a plurality of focus evaluation values, wherein each of the plurality of focus evaluation values indicates a focus state of a corresponding lens of a plurality of lenses;
a selection unit configured to select a reference lens from the plurality of lenses; and
a movement control unit configured to:
determine a first lens movement parameter based on a first focus evaluation value of the plurality of focus evaluation values;
determine a second lens movement parameter based on a second focus evaluation value of the plurality of focus evaluation values, wherein
the evaluation value calculation unit is further configured to calculate the second focus evaluation value based on the first focus evaluation value,
the first focus evaluation value corresponds to the selected reference lens,
the second focus evaluation value corresponds to a lens of the plurality of lenses, and
the lens is different from the selected reference lens;
calculate a weighted average of the first lens movement parameter and the second lens movement parameter; and
determine a common lens movement parameter based on the weighted average of the first lens movement parameter and the second lens movement parameter, wherein the common lens movement parameter is common to each of the plurality of lenses.

13. A medical observation device, comprising:
an evaluation value calculation unit configured to calculate a plurality of focus evaluation values, wherein each of the plurality of focus evaluation values indicates a focus state of a corresponding lens of a plurality of lenses; and
a movement control unit configured to:
determine a plurality of lens movement parameters corresponding to the plurality of lenses based on the plurality of focus evaluation values of the plurality of lenses;
determine an average value of the plurality of lens movement parameters; and
determine a common lens movement parameter based on the average value of the plurality of lens movement parameters, wherein the common lens movement parameter is common to each of the plurality of lenses.

* * * * *